(12) United States Patent
Oz et al.

(10) Patent No.: US 12,016,629 B2
(45) Date of Patent: *Jun. 25, 2024

(54) SCREENING APPARATUS AND METHOD

(71) Applicant: NOVA-SIGHT LTD., Airport City (IL)

(72) Inventors: Dan Oz, Airport City (IL); Michael Belkin, Airport City (IL); Ran Yam, Airport City (IL); Oren Yehezkel, Airport City (IL)

(73) Assignee: NOVA-SIGHT LTD., Airport City (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/940,477

(22) Filed: Sep. 8, 2022

(65) Prior Publication Data

US 2023/0000345 A1 Jan. 5, 2023

Related U.S. Application Data

(63) Continuation of application No. 17/336,354, filed on Jun. 2, 2021, now Pat. No. 11,678,795, which is a
(Continued)

(51) Int. Cl.
*A61B 3/113* (2006.01)
*A61B 3/08* (2006.01)
(Continued)

(52) U.S. Cl.
CPC ............... *A61B 3/113* (2013.01); *A61B 3/08* (2013.01); *A61B 3/145* (2013.01); *A61H 5/005* (2013.01);
(Continued)

(58) Field of Classification Search
CPC ......... A61B 3/0025; A61B 3/08; A61B 3/085; A61B 3/113; A61B 3/145; A61B 5/0036;
(Continued)

(56) References Cited

U.S. PATENT DOCUMENTS 9,844,317 B2 * 12/2017 Green .................... A61B 3/032
2015/0257967 A1 * 9/2015 Simmons ............... G16H 50/20
434/236
(Continued)

*Primary Examiner* — Mustak Choudhury
(74) *Attorney, Agent, or Firm* — The Law Office of Joseph L. Felber

(57) ABSTRACT

An apparatus for screening, treatment, monitoring and/or assessment of visual impairments, comprising electronic means for simultaneously applying two separate and unrelated processing methods to images presented to a patient's eyes: a first processing method being applied to an non-amblyopic eye (the eye with the better vision), and a second processing method being applied to an amblyopic eye (the weaker eye, or the impaired eye). A method for screening, treatment, monitoring and/or assessment of visual impairments, comprising: a. defining a starting point, wherein differences between a patient's eyes are completely, or as closely as practically possible, corrected, to enable two identical or similar images to be transferred to the brain from the patient's eyes; b. defining an ending point, wherein there is no correction applied to any of the patient's eyes; c. defining a screening, treatment, monitoring and/or assessment plan, for initially applying correction to images according to the starting point, then gradually reducing the correction, at a controlled and predetermined rate, towards the ending point; and d. applying the plan to images presented to the patient's eyes, while monitoring patient's performance.

13 Claims, 29 Drawing Sheets

Related U.S. Application Data continuation of application No. 16/334,666, filed as application No. PCT/IL2017/051063 on Sep. 24, 2017, now Pat. No. 11,064,882.

(60) Provisional application No. 62/398,532, filed on Sep. 23, 2016.

(51) Int. Cl.
*A61B 3/14* (2006.01)
*A61H 5/00* (2006.01)

(52) U.S. Cl.
CPC .............. *A61H 2201/0157* (2013.01); *A61H 2201/0192* (2013.01); *A61H 2201/1207* (2013.01); *A61H 2201/165* (2013.01); *A61H 2201/50* (2013.01); *A61H 2205/024* (2013.01)

(58) Field of Classification Search
CPC ......... A61B 5/0058; A61B 5/16; A61B 5/163; A61B 5/168; A61B 5/4836; A61H 5/005; A61H 2201/1207; A61H 2201/1604; A61H 2201/5043; A61H 2201/5007; A61H 2201/5092; A61H 2201/0157; A61H 2201/0192; A61H 2201/50; A61H 2201/165; A61H 2205/024; G16H 50/20; G16H 50/30

See application file for complete search history.

(56) References Cited

U.S. PATENT DOCUMENTS

| | | | |
|---|---|---|---|
| 2016/0037137 A1* | 2/2016 | Seiflein | G09B 21/006 348/158 |
| 2016/0270656 A1* | 9/2016 | Samec | A61B 3/1216 |
| 2017/0263107 A1* | 9/2017 | Doyle | G08B 25/08 |
| 2018/0168444 A1* | 6/2018 | Foss | A61B 3/113 |

\* cited by examiner

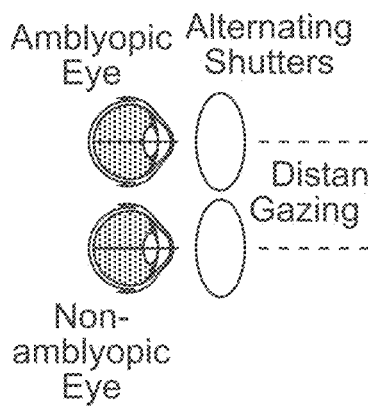 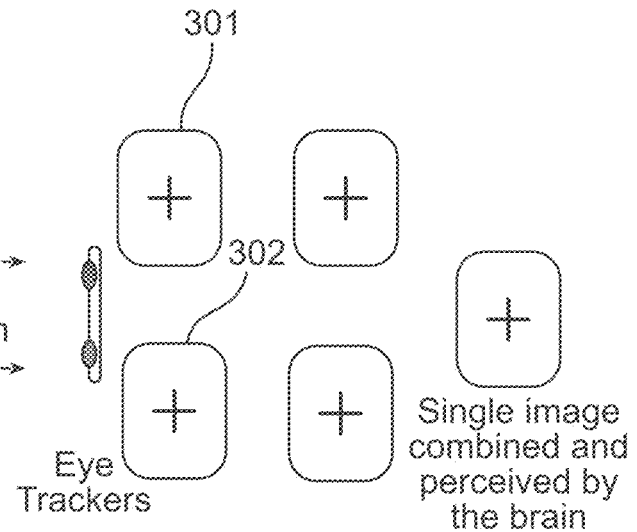
FIG. 15A    FIG. 15B
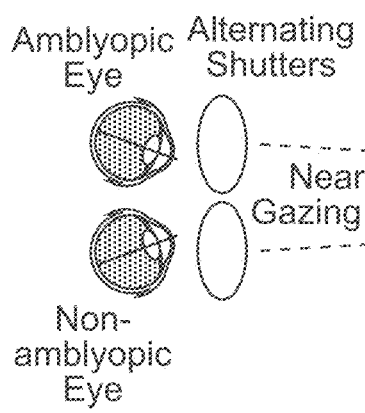 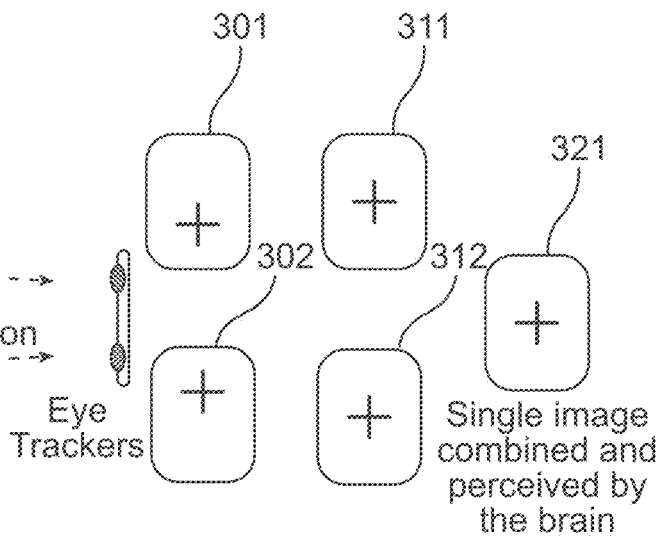
FIG. 16A    FIG. 16B

SCREENING APPARATUS AND METHOD

This application is a Continuation of U.S. Ser. No. 17/336,354 filed Jun. 2, 2021 which is a Continuation of U.S. Ser. No. 16/334,666 filed Mar. 19, 2019 which is a 371 of PCT/IL2017/051063 having an International Filing Date of Sep. 24, 2017 which was published on Mar. 29, 2018 as WO2018/055618 which is included by reference as if fully set-forth herein. The present application claims the benefit of Provisional Patent Application No. 62/398,532 filed on Sep. 23, 2016 which is included by reference as if fully set-forth herein.

TECHNICAL FIELD

The present invention relates to visual impairments caused by eye and neural diseases and more specifically to an apparatus and method for screening, treatment, monitoring and assessment of visual impairments.

DESCRIPTION OF RELATED ART

Prior Art Patents and Applications

Hess et al., U.S. Pat. No. 8,057,036—Binocular vision assessment and/or therapy.
Evans et al., US 20130258463—System, method, and apparatus for enhancing stereoscopic images.
Vendel et al., U.S. Pat. No. 8,770,750—Apparatus and method for establishing and/or improving binocular vision.
Avni et al., WO 2014/041545—Systems and methods for treating amblyopia by visual stimulation of the brain.
Fateh, U.S. Pat. No. 8,820,930—System, method and apparatus for amblyopia and ocular deviation correction.
Foss, WO 2015/145111—Apparatus and methods for the treatment of ocular disorders.

Amblyopia

Amblyopia is a developmental disorder of spatial vision usually associated with the presence of strabismus, anisometropia or vision form deprivation early in life. It affects visual acuity, contrast sensitivity and depth perception and, if not timely treated properly, might result permanent reduction of visual capacity of the amblyopic eye. Amblyopia is clinically important because it prevents the visual apparatus from developing normally and it is the most frequent cause of vision loss in infants and young children; About 4% of children and 2% of adults suffer from amblyopia.

In healthy individuals, two slightly different images are transferred from both eyes to the brain which fuses these two images into a composite, single, 3-dimensional image.

Sometimes, however, the image arriving from one eye significantly differs from that arriving from the other eye. This can be caused by a variety of factors, such as the eyes not being parallel (strabismus), one eye being more far or short sighted than the other (anisometropia), or diseases that create abnormal images in an eye of a child (such as a cataract or other media opacity). Such conditions in adults lead to double or blurry vision. However, the child's brain can avoid such disturbing sensation by disregarding the image from one eye. If this condition is not successfully treated during childhood, the person will become permanently amblyopic, i.e. the brain ignores the image from the amblyopic eye and this eye will have poorer vision then the other one. Normally there is no spontaneous improvement in the vision of the amblyopic eye and in about half of the cases there is deterioration after diagnosis.

Stereoscopic vision will not develop properly or not at all in amblyopic people, even if successfully treated on time; they are incapable of precise stereoscopic vision and consequently of depth perception. Amblyopic people are thus limited in their career choice in addition to being worried about having only one fully functional eye, more liable to lose the seeing eye and suffering more commonly from a variety of psychological conditions.

It was found in a survey of adult amblyopes (without strabismus) that they felt that the diseases interfered with school (52%), interfered with their work (48%), affected their lifestyle (50%), affected their sport participation (40%) and influenced their career choice (36%). These patients were found to have a significantly greater degree than normal of somatization, obsessive-compulsive behavior, excessive interpersonal sensitivity and anxiety.

Convergence Insufficiency (CI)

Convergence insufficiency is a common near vision problem that interferes with a person's ability to see, read, learn, and work at near distances.

Signs and symptoms occur while the child is reading or engaged in other near field activities and may include eyestrain, headaches, difficulty reading, double vision, difficulty concentrating, squinting or closing one eye.

Children with CI have more symptoms and show worse attention when reading than children without CI. This might make parents or teachers suspect that a child has a learning disability, instead of an eye disorder.

The problem exists in adults as well, especially the people who spend a considerable time looking at near objects such as computer screens.

Other Ailments

Many other eyes' deficiencies exist such as visual acuity decrements, strabismus (either tropia and phoria), stereopsis acuity, color blindness and various eye dynamics ailments. They effect many children and if not treated early in life, become incurable.

Current Amblyopia Treatments

Amblyopia is treated by forcing the use of the amblyopic eye by preventing the non-amblyopic eye from seeing or reducing the quality of vision in that eye. Treatment of amblyopia is effective only in children up to the age of nine or younger. There are several ways, or combinations thereof, to perform the treatment detailed below.

Occluding the Dominant Eye by Patching, Electronic Shutters, Blurred Lens, Etc.

Occlusion of the dominant eye (good eye) is a long-established method and produces positive results in many cases, but only when there is a good compliance with the treatment. However, patching has many drawbacks, mainly the impaired visual functions engendered by covering the better-seeing eye in children, as well as the social and emotional problems related to wearing an unsightly eye-patch. As a result of all these factors, compliance with eye patching is limited and many children reach the critical age of nine with reduced vision in the affected eye that is considered to be incurable.

Furthermore, since the patching method stimulate alternately only one eye at a time, the stereopsis process in the visual cortex is not challenged and therefor deteriorates or no developing at the first place, disabling the patient from 3-dimension perception even if good visual acuity is attained in both eyes separately.

In addition, a child suffering from strabismic amblyopia will be referred to a strabismus surgery. However, since eyes are not used to work together, even after the surgery the tendency of the eyes to move synchronously is weak, and the eyes might misalign again even if the surgery was a successful one and patching therapy was practiced prior to the surgery.

Atropine Penalization

Atropine is instilled into the non-amblyopic eye and causes pupillary dilation and reduced accommodation subsequently forcing the amblyopic eye to be used for near-vision tasks. This treatment can cause reverse amblyopia. Further disadvantages are the pupillary dilatation in the treated eye causing light sensitivity, lack of development of stereopsis and irregular compliance.

Correction of Refractive Errors

This method is used for corrections of anisometropic amblyopia by equalizing the size and sharpness of the images on both eyes. This therapy can't be used to treat strabismic amblyopia and is effective only if undertaken in time. The latter is problematic, since, unlike strabismus, there are no apparent symptoms of the condition.

Dichoptic Eyes Stimulation

This method was introduced in recent years and provide different images to both eyes, introducing a better image quality for the amblyopic eye while providing a degraded image for the fellow eye.

The pictures are presented either on 3D PC monitors or on head-mounted displays.

However, this method does not ensure the simultaneous and accurate foveal stimulation for strabismic patient, especially when the deviation angle between the two eyes is not constant for different gazing angles. Furthermore, it's nearly impossible to calibrate the apparatus to compensate for heterophoria.

Perceptual Learning

Perceptual learning—a process by which the ability of sensory apparatus to respond to stimuli is improved through experience. Perceptual learning occurs through sensory interaction with the environment as well as through practice in performing specific sensory tasks. The changes that take place in sensory and perceptual apparatus as a result of perceptual learning occur at the levels of behavior and physiology. Perceptual learning involves relatively long-lasting changes to an organism's perceptual apparatus that improve its ability to respond to its environment.

Studies showed that perceptual learning provide an important method for treating amblyopia. Practicing a visual task results in a long-lasting improvement in performance in an amblyopic eye. The improvement is generally strongest for the trained eye, task, stimulus and orientation, but appears to have a broader spatial frequency bandwidth than in normal vision. Importantly, practicing on a variety of different tasks and stimuli seems to transfer to improve visual acuity.

One major drawback of the methods above is that the eyes are stimulated one at a time thus providing the brain with monocular images and preventing to exercise the stereopsis process performed in the visual cortex of the brain. Thus, depth perception is degenerated.

The success rate in childhood amblyopia treatment is about 50% [reaching vision better than 6/9 (20/30)] and is better in anisometropic than in strabismic amblyopia. This is the only amblyopia treatment which is at least partially successful in adults. However, it requires long duration of repeated perceptual training and thus is limited by low compliance which causes it not to become a regular amblyopia treatment.

Treatment of the amblyopia should always be combined with treatment of its cause, i.e. surgery for the strabismus, optical correction for the anisometropia and removal of the causes of unequal vision. Even when successful treatment took place during the critical period in children under nine years of age, the results are not permanent and about half of the patients deteriorate and may require maintenance therapy. Furthermore, deterioration of the surgically corrected strabismus often occurs as there is no stereoscopic vision which helps to keep the optical axes aligned.

As a consequence of the relative ineffectiveness of the present-day treatment of childhood amblyopia and the difficulty of diagnosing the disease when it is still treatable, 2% to 4% of the adult population in all countries is amblyopic.

Amblyopia is considered untreatable in people older than 9 years. However, recent studies suggest that adult amblyopia is treatable—as can be learned from the success of perceptual learning, proving that the neural pathways, presumed lost for the amblyopic eye can be used for treatment in adults. This modality involves continuous tedious ocular exercises and is therefore rather impractical.

Prior Art Convergence Insufficiency Treatment

Treatments range from passive prism lenses to active office-based vision therapy. Scientific research by the National Eye Institute has proven that office-based vision therapy is the most successful treatment.

Home-based pencil pushups therapy appears to be the most commonly prescribed treatment, but scientific studies have shown that this treatment is ineffective.

Even though these methods are quite simple, the requirement of occasional visit at the doctor's office is cumbersome while the home base pencil pushups therapy is boring for the child and have a low compliance.

In addition, in both methods, real time monitoring of the progress of the child to track the stimulus does not exist, therefore feedback for the therapist and parents is unavailable nor a real time feedback for the child that might stimulate him to improve his exercises.

Prior Art Eyes' Monitoring And Assessment Methods

Current approaches are performed by specialists—either ophthalmologists, orthoptists or optometrists and require procedures that are time consuming and expensive.

Visual acuity, strabismus and heterophoria, stereopsis depth and eyes' dynamic tests are standard and routine tests. However, they require patient cooperation which is difficult or even impossible to perform on toddlers.

Those tests are important factors in providing the ability to detect amblyopia (and other malfunctions of the eye) and to assess the progress in the amblyopia treatment.

These and other problems in prior art methods and apparatu for Screening, Diagnosing, Assessing, Monitoring and Treating Eye Diseases and Visual Impairments Using Eye Tracking are addressed with the present invention.

SUMMARY OF THE INVENTION

The present invention relates to an apparatus and method for Screening, Diagnosing, Assessing, Monitoring and Treating Eye Diseases and Visual Impairments, such as amblyopia and strabismus.

The main features and benefits of the present invention are:
1. An apparatus for measuring and/or treating a vision-related disease, using two separate and unrelated processing methods being simultaneously applied to the patient's eyes. For example, the image presented to each of patient's two eyes undergoes a different processing:

a. For the non-amblyopic eye, the processing includes an area with a controlled measure of image degradation, to cause the patient to rely more on the other, weaker eye; furthermore, the location of the degraded area is moved on the screen responsive to the measured direction of the line of sight of the non-amblyopic eye;

b. For the amblyopic eye, the processing includes changing the image so as to present identical, real 3D disparity or as similar as possible images to the two eyes, to allow combining the images in the brain.

Processing may include a movement of the image vertically and/or horizontally, changing the magnification of the image (zoom in or zoom out), and/or rotation of the image.

The processing is responsive to the measured direction of the line of sight of the amblyopic eye- That is, as the line of sight moves vertically and/or horizontally and/or torsionally, so the presented image on the screen is moved as well.

2. "On the go" real time treatment. The patient can receive treatment as he works, walk, during recreation, etc. The patient wears goggles with means for capturing real-time images, a processor for processing the image to one eye or both according to predefined settings adapted to that patient's ilness, and display means for presenting the processed image(s) to the patient's eye(s). This embodiment may save patient's time, and is easier to perform. Rather than visiting a clinic, waiting and receiving treatment, the patient receives treatment while he/she is doing other tasks.

3. Using true tri-dimensional (3D) images for measurement and treatment. True 3D images best stimulate the brain to combine the images, so the patient perceives the depth of each object in space—an essential benefit, which people with normal healthy vision may fail to fully appreciate.

Presenting exact identical images to both eyes will preserve binocular vision, however, stereopsis (3D process) in the cortex will not be challenged and 3D perception will not be enhanced. 3D perception is a precious and frangible skill, which can be easily lost when there are vision problems. The present invention uses an innovative concept to achieve this benefit, including:

a. Using true 3D images, that is images generated from two cameras, separately located so they will "see" the world just like two normal eyes, which are separately located, would see the world. The images from the two cameras are not identical but contain some tiny differences; these differences are used by the brain to reconstruct and perceive the 3D scene.

b. Correcting the defects of the weak eye by processing the image presented thereto, so the brain will perceive identical, or as close to identical as possible, images from the two eyes; this allows the brain to combine the two images into one object. A digital processor is used to change the image to one eye by moving of the image vertically and/or horizontally, changing the magnification of the image (zoom in or zoom out), and/or rotating the image.

c. Challenging/stimulating the patient to rely more on the weaker eye, by a controlled degradation of the image presented to the stronger (better vision) eye.

4. The above main features (1-3) can be combined in many variations, and the parameters of the digital processing may be adjusted so as to best fit the visual problems of each patient.

The apparatus in the present invention is modular and flexible; it is software-controlled, to achieve a very powerful and useful apparatus for Screening, Diagnosing, Assessing, Monitoring and Treating Eye Diseases and Visual Impairments.

Notes:
1. It is essential to distinguish between
(a) Using true tri-dimensional (3D) images for measurement and treatment, on the one hand, and (b) 3D display devices, such as 3D monitors, 3D glasses, etc. The feature (a) is an essential part of the present invention, and relates to 3D images creation, separate processing for each eye and separate display to each eye;

Whereas (b) relates to prior art equipment for presenting separate images to each eye.

The present invention uses 3D devices (b) to present a different, separate image to each eye; but this is just one component of the apparatus and method presented in (a).

2. Contemporary digital processors offer means for powerful image processing, in small packages and at low cost. This facilitates making a portable, "On-the-go" apparatus.

One example of such a processor is the 32 bit PIC32MZ Family of High performance microcontrollers with Floating point Unit (FPU) and an advanced peripheral set, manufactured by Microchip Technology Inc.

According to aspect of some embodiments of the invention, there is also provided an apparatus for screening, treatment, monitoring and/or assessment of visual impairments, comprising electronic means for simultaneously applying two separate and unrelated processing methods to images presented to a patient's eyes: a first processing method being applied to an non-amblyopic eye (the eye with the better vision), and a second processing method being applied to an amblyopic eye (the weaker eye, or the impaired eye).

In some embodiments, the electronic means comprise images generating means, digital image processing means, eye tracker means for measuring a direction of the patient eyes' line of sight, and display means for presenting images to at least one of the patient's eyes.

In some embodiments, the apparatus is stationary and is based on a desktop or a laptop personal computer (PC).

In some embodiments, the apparatus is portable and is based on a tablet or smart phone.

In some embodiments, the apparatus is portable and is based on wearable goggles, wherein the display means comprise micro-displays mounted on the goggles, and further including a digital processor for control and images processing.

In some embodiments, the first processing method creates an area with a controlled measure of image degradation.

In some embodiments, the the area with image degradation is so located on the display as to be presented on a fovea of the non-amblyopic eye.

In some embodiments, the area with image degradation is so located on the display as to be presented on a macula of the non-amblyopic eye.

In some embodiments, the apparatus further includes means for using the measured direction of sight of the non-amblyopic eye for presenting the area with image degradation on the fovea or the macula of the non-amblyopic eye.

In some embodiments, the second processing method includes changing the image so as to present identical, real 3D disparity or as similar as possible images to the two eyes, to allow combining the images in the brain. In some such embodiments, the second processing method includes a movement of the image vertically and/or horizontally, changing the magnification of the image (zoom in or zoom out), and/or rotation of the image.

In some embodiments, the second processing method is responsive to a measured direction of a line of sight of the amblyopic eye. In some embodiments, the apparatus further usies the eye tracker means for measuring the the line of sight of the amblyopic eye.

According to aspect of some embodiments of the invention, there is also provided an apparatus for screening, treatment, monitoring and/or assessment of visual impairments, comprising wearable goggles with a camera, digital processor means and a micro display mounted on the goggles, and wherein the camera captures real time images of the area the goggles point at to generate a video signal which is transferred to the processor, and the processor applies a digital processing to the video for one eye or both according to predefined settings adapted to that patient's ilness, and the display means present the processed image(s) to the patient's eye(s). In some embodiments, the apparatus further includes eye tracker means for measuring the direction of the line of sight of the patient's eyes and transferring the results to the processor, and wherein the digital processing is responsive to the eye tracker measurements.

According to aspect of some embodiments of the invention, there is also provided an apparatus for screening, treatment, monitoring and/or assessment of visual impairments, comprising means for generating true tri-dimensional (3D) images, digital image processing means, eye tracker means for measuring a direction of the patient eyes' line of sight, and display means for presenting images to at least one of the patient's eyes.

In some embodiments, the means for generating true tri-dimensional (3D) images comprise two cameras, both pointing generally in the same direction and displaced laterally from each other.

In some embodiments, the means for generating true tri-dimensional (3D) images comprise two cameras, both pointing generally in the same direction and each mounted near one of a patient's eyes on wearable goggles.

In some embodiments, the means for generating true tri-dimensional (3D) images comprise one camera, mounted near one of a patient's eyes on wearable goggles, and wherein the goggles allow an other eye of the patient to look at a surroundings.

In some embodiments, the digital processing means comprise means for changing the image presented to the non-amblyopic eye so as to present identical, real 3D disparity or as similar as possible images to the two eyes, to allow combining the images in the brain. In some such embodiments, the digital processing includes a movement of the image vertically and/or horizontally, changing the magnification of the image (zoom in or zoom out), and/or rotation of the image.

In some embodiments, the digital processing is responsive to a measured direction of a line of sight of the amblyopic eye.

According to aspect of some embodiments of the invention, there is also provided a method for screening, treatment, monitoring and/or assessment of visual impairments, comprising:
a. defining a starting point, wherein differences between a patient's eyes are completely, or as closely as practically possible, corrected, to enable two identical or similar images to be transferred to the brain from the patient's eyes;
b. defining an ending point, wherein there is no correction applied to any of the patient's eyes;
c. defining a screening, treatment, monitoring and/or assessment plan, for initially applying correction to images according to the starting point, then gradually reducing the correction, at a controlled and predetermined rate, towards the ending point; and
d. applying the plan to images presented to the patient's eyes, while monitoring patient's performance.

In some embodiments, the method further includes the step of adjusting the rate of change of the correction responsive to results of monitoring the patient's performance.

In some embodiments of the method, the correction includes a movement of the image vertically and/or horizontally, changing the magnification of the image (zoom in or zoom out), and/or rotation of the image.

In some embodiments of the method, while changing the plan for screening, treatment, monitoring and/or assessment responsive to results of monitoring the patient's response to applying the plan thereto.

In some embodiments the method further includes the steps of defining a range of desired rate of improvement with minima and maxima, during monitoring comparing actual patient's performance with the desired rate of improvement, and issuing a report or a warning if the actual performance exceeds the range of desired rate of improvement.

Further Features and Benefits of the Invention

One of the goals of the apparatus is to treat amblyopia by preserving and improving the visual acuity of the amblyopic eye while preserving and enhancing the depth perception of the patient.
General:
  Each of the presented embodiments examples work for all described tasks
  The description provides examples of stationary and portable apparatus
  Adjustable for near or far vision treatment by adjusting properly the accommodation and convergence parameters
  Eye trackers will track the eyes and verify whether the eyes track the presented object
Amblyopia Treatments
  Providing dichoptic images (different images to each eye) either stationary, or dynamic in the form of movies, games, animations etc. thus exercising the stereopsis process in the brain. The 2 images can be identical or have disparity properties for providing real depth sensation for better enhancement of the stereopsis process, and strabismus compensation.
  In case of strabismic amblyopia (most difficult type of amblyopia to overcome) the suggested apparatus would be the only solution that enables a binocular, clear fused image on the retinas even if strabismus angles change with different gaze directions. This compensation will be implemented by the real-time image disparity compensation based on the live eye tracking data.
  The nature of the images will be different in such a way as to challenge the brain to prefer the use the amblyopic eye while stimulating also the fellow eye (even with reduced or partial image quality) thus exercising the related brain pathways in charge of the visual information received from the amblyopic eye, and encouraging the stereopsis process in the visual cortex of the brain.
  Inherent capability for treating also anisometropic amblyopia by providing different sized images to each eye.
  A single or multiple eye trackers (an existing technology) will ensure the coherence projection of the 2 images on the fovea regions of the 2 eyes according to the instantaneous gazing direction for all conditions of asymmetric eye movements, including torsional deviation.
  For portable goggles, images can be provided by one or two scene cameras allowing "on the go" treatments.

Ability to train vision in both near field and far field.

Automatic progress monitoring and assessment using the eye tracking feedback.

Convergence Deficiency Diagnosis & Treatment

Providing a single image or dichoptic images (different images to each eye) either stationary, or dynamic in the form of movies, games, animations etc. The 2 images can coincide or have disparity properties for providing real depth sensation for better enhancement of the stereopsis process and strabismus compensation.

The 2 images are automatically moving towards each other and even to opposite sides of the screen so as to challenge the eyes of the patient to converge.

The eye trackers will verify whether the eyes are properly tracking the inward moving targets.

This exercise will be presented to the child in a gradual manner and the progress will be monitored, evaluated and changed according the progress and training program thus providing valuable feedback to the practitioner and parents and allows for a bio-feedback for the child.

Eyes Coordination Deficiency

Providing a single image or dichoptic images (different images to each eye) either stationary, or dynamic in the form of movies, games, animations etc.

The 2 images can coincide or may have disparity properties for providing real depth sensation for better enhancement of the stereopsis process and strabismus compensation The single or separate 2 images include dynamic stimulus at predefined speeds and paths as to train and monitor the ocular muscles to work separately and as a team.

The eye trackers will verify whether the eyes are properly tracking the stimulus.

This exercise will be presented to the child in a gradual manner and the progress will be monitored, evaluated and changed according the progress and training program thus providing valuable feedback to the practitioner and parents and allows for a bio-feedback for the child.

Monitoring and Assessment

The apparatus measures, during normal training various parameters and asseses various visual performances of the eyes.

Important benefits: All the tests can be conducted even on pre-school children, since these tests do not require any voluntary feedback from the child or cooperation therewith. Following are examples of tests that can be performed continuously or periodically:

Visual acuity and contrast sensitivity

Strabismus angles and extent of heterophoria

Convergence deficiency

Eye movements: saccades speeds, trajectory and reaction time

Depth perception and stereopsis quality

Pupil diameter and responses

Based on above, the apparatus analyzes the measured data, assesses the progress based on comparison with past patient data or with a standard model and:

Changes the treatment program

Provides alerts and reports to the doctor, patient or patient's relatives

Provides a bio-feedback to the child

Screening

For screening, the apparatus performs the same measurements as for monitoring and assessment, compares it to standard data for reporting of possible problems that requires more thorough examination by a specialist.

Since screening requires a less accurate level of results, a higher threshold might be used with a faster test sequence and lower cost apparatus.

Since all the above testing are automatic and fast, the screening procedures can be performed by a technician, school nurse and others. The tests do not necessary require a specialist such as an ophthalmologist or optometrist.

Amblyopia condition, which must be detected as early as possible and is the most common and dangerous problems in young, even preverbal children, will thus be easily detected (with all or some of the tests). Appropriate referral to the specialist will be generated and reduce the existing high "false positive" rate, which have a significant burden on the eye care apparatus, and reduce the "false negative" rate that fails to detect many children and causes them incurable, severe eye problems.

As detailed in the present disclosure, the invention overcomes the disadvantages of the existing treatments methods and devices, is easily performed, and is attractive to the children.

The monitoring, assessment and screening, need minimal child cooperation and can be performed in a matter of minutes or even seconds.

Further purposes and benefits of the current invention will become apparent to persons skilled in the art upon reading the present disclosure and the related drawings.

BRIEF DESCRIPTION OF THE DRAWINGS

Embodiments of the invention are disclosed hereinafter with reference to the drawings, in which:

FIGS. 15A, 15B show non strabismic eyes, far vision.

FIGS. 16A, 16B show non strabismic eyes, near vision.

FIGS. 36A, 36B show a Method of Target Stimulus for Saccades Test.

DETAILED DESCRIPTION OF THE INVENTION

Figure 1:
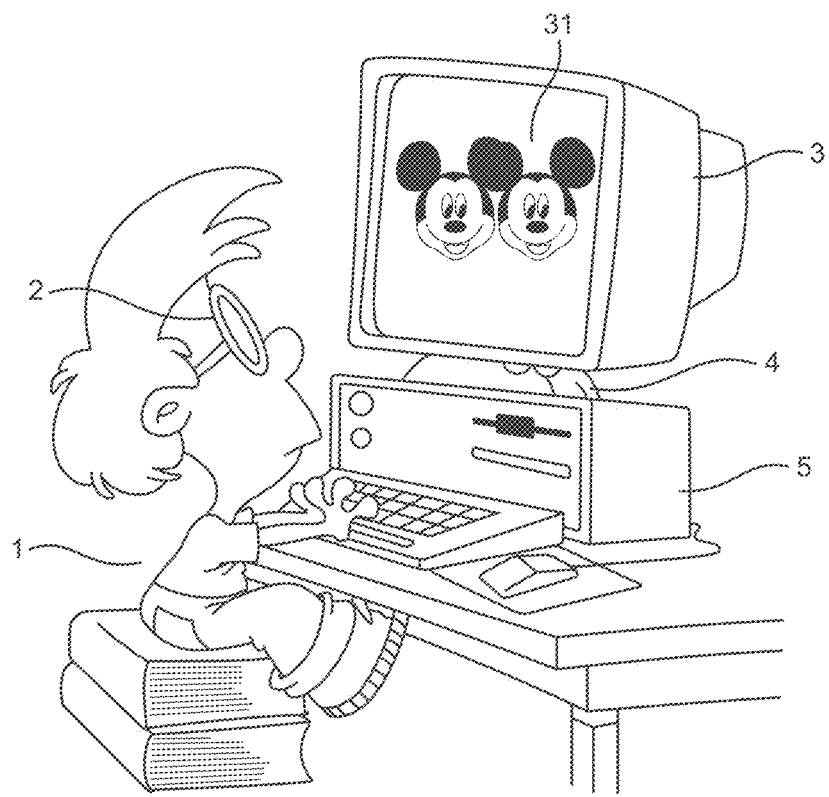
FIG. 1 shows a Stationary apparatus, a General View.

The current invention will now be described by way of example and with reference to the accompanying drawings. Remarks:
- a. The 3D monitor and glasses can be of any kind—e.g. passive, alternating, polarized etc.
- b. Monitor=display=screen (Stationary apparatus—one 3D display; Portable apparatus—one or two microdisplays)
- c. 3D=three-dimensional
- d. Near eye display=micro display
- e. Fellow eye=non amblyopic eye (the better, stronger eye).

A Apparatus for Simultaneously Measuring and Treating One or More Vision-Related Diseases, Using Separate Processing Methods for Each Eye For example, the image presented to each of patient's two eyes undergoes a different processing:
- a. For the non-amblyopic eye, the processing includes an area with a controlled measure of image degradation, to cause the patient to rely more on the other, weaker eye; furthermore, the location of the degraded area is moved on the screen responsive to the measured direction of the line of sight of the non-amblyopic eye;
- b. For the amblyopic eye, the processing includes changing the image so as to present identical or as similar as possible images to the two eyes, to allow combining the images in the brain.

Processing may include a movement of the image vertically and/or horizontally, changing the magnification of the image (zoom in or zoom out), and/or rotation of the image.

The processing is responsive to the measured direction of the line of sight of the amblyopic eye- That is, as the line of sight moves vertically and/or horizontally, so the presented image on the screen is moved as well.

Gradual image degradation: for the non-amblyopic eye, the measure of image degradation needs not be uniform in the area with image degradation; preferably, the degradation is stronger in the center of that area, and is gradually reduced toward the edges of the area, to provide a smooth transition.

"On the Go" Real Time Treatment

The patient can receive treatment as he works, during recreation, etc. The patient wears goggles with means for capturing real-time images, a processor for processing the image to one eye or both according to predefined settings adapted to that patient's ilness, and display means for presenting the processed image(s) to the patient's eye(s). This embodiment may save patient's time, and is easier to perform. Rather than visiting a clinic, waiting and receiving treatment, the patient receives treatment while he/she is doing other tasks.

Using True Tri-Dimensional (3D) Images for Measurement and Treatment

True 3D images best stimulate the brain to combine the images, so the patient perceives the depth of each object in space—an essential benefit, which people with normal healthy vision may fail to fully appreciate. 3D perception is a precious and frangible skill, which can be easily lost when there are vision problems.

The present invention uses an innovative concept to achieve this benefit, including:
- a. Using true 3D images, that is images generated from two cameras, separately located so they will "see" the world just like two normal eyes, which are separately located, would see the world. The images from the two cameras are not identical but contain some tiny differences; these differences are used by the brain to reconstruct the 3D scene.

b. Correcting the defects of the weak eye by processing the image presented thereto, so the brain will perceive identical, or as close to identical as possible, images from the two eyes; this allows the brain to combine the two images into one 3D object.

A digital processor is used to change the image to one eye by moving of the image vertically and/or horizontally, changing the magnification of the image (zoom in or zoom out), and/or rotating the image.

c. Challenging/stimulating the patient to rely more on the weaker eye, by a controlled degradation of the image presented to the stronger (better vision) eye.

Adaptive Method for Screening, Treatment, Monitoring and/or Assessment of Visual Impairments The method includes:
 a. defining a starting point, wherein differences between a patient's eyes are completely, or as closely as practically possible, corrected, to enable two identical or similar images to be transferred to the brain from the patient's eyes;
 b. defining an ending point, wherein there is no correction applied to any of the patient's eyes;
 c. defining a screening, treatment, monitoring and/or assessment plan, for initially applying correction to images according to the starting point, then gradually reducing the correction, at a controlled and predetermined rate, towards the ending point; and
 d. applying the plan to images presented to the patient's eyes, while monitoring patient's performance;
 e. adjusting the rate of change of the correction responsive to results of monitoring the patient's performance;
 f. defining a range of desired rate of improvement with minima and maxima, during monitoring comparing actual patient's performance with the desired rate of improvement, and issuing a report or a warning if the actual performance exceeds the range of desired rate of improvement.

The Above Method can be Applied to any of the Embodiments of the Apparatus Disclosed in the Present Invention. Combining the Above Main Features in Many Variations, and Adjusting the Parameters of the Digital Processing, so as to Best Fit the Visual Problems of Each Patient The apparatus in the present invention is modular and flexible; it is software-controlled, to achieve a very powerful and useful apparatus for Screening, Diagnosing, Assessing, Monitoring and Treating Eye Diseases and Visual Impairments.

Notes:
1. It is essential to distinguish between
   (a) Using true tri-dimensional (3D) images for measurement and treatment, on the one hand, and
   (b) 3D display devices, such as 3D glasses, etc.

The feature (a) is an essential part of the present invention, and relates to 3D images creation, separate processing for each eye and separate display to each eye;

Whereas (b) relates to prior art equipment for presenting separate images to each eye.

The present invention uses 3D devices in (b) to present a different, separate image to each eye; but this is just one component of the apparatus and method presented in (a).

2. Contemporary digital processors offer means for powerful image processing, in small packages and at low cost. This facilitates making a portable, "On-the-go" apparatus.

One example of such a processor is the 32 bit PIC32MZ Family of High performance microcontroller with Floating point Unit (FPU) and an advanced peripheral set, manufactured by Microchip Technology Inc.

Hardware

We will describe here examples of 3 embodiments, all based on similar principles and sub-assemblies:
 Stationary Apparatus based on PC, laptop etc., for home or office use;
 Portable apparatus based on tablet, smart phone etc. for home, office or screening;
 Portable apparatus based on goggles with micro-displays for home, office or "on the go" use.

In all the embodiments, either stationary or portable, corrective lenses, if required, might be added. In the portable apparatus based on goggles, a special fitting for the addition of corrective lenses might be added to the goggles frame or directly integrated into the provided eye pieces' lenses.

In addition, the images will be provided separately for both eyes in such accommodation/convergence properties as required for near or far vision. The principle of operation is as described in our international patent application No. PCT/IL2016/050232.

In addition, a microphone can be added with appropriate voice recognition software for getting patient response to various stimuli, measurements of reading speeds etc. The microphone is depicted only in FIG. 2 but similarly can be added to all embodiments.

Stationary Apparatus

FIG. 1 shows a Stationary Apparatus, comprising: 3D glasses 2 (alternating shutter glasses in this example), a 3D display or monitor 3, a remote eye tracker 4 located near the display or a close-by eye tracker mounted on the glasses frame, and a personal computer (PC) or a digital processor 5.

Also shown are a patient 1 and two dichoptic images 31.

Figure 2:
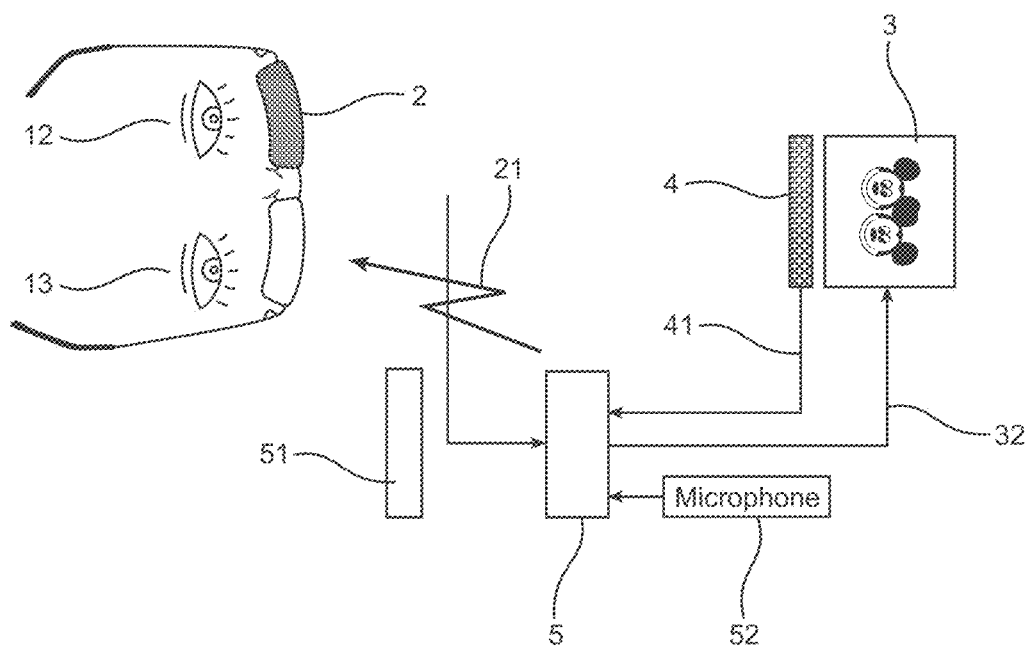
FIG. 2 shows a Stationary apparatus, a Block Diagram.

The apparatus block diagram is depicted in FIG. 2, and includes: A personal computer (PC) or a digital processor 5, 3D glasses 2 with 3D glasses controls 21, control inputs (i.e. keyboard, mouse, tablet, etc.) 51, a microphone 52, remote eye tracker 4 and 3D display 3.

Also shown are the eye tracker data 41, display signals 32, patient's left eye 13 and right eye 12. The processor 5 controls the 3D glasses 2 (if required) and sends the required and processed two dichoptic images (either stationary pictures, video, games etc.) to the 3D display 3. In addition, the processor receives the eyes' gazing direction from the eye tracker 4 and all required controls from the input devices such as the keyboard, mouse etc.

Portable Apparatus Based on Tablet

Instead of a PC, the apparatus can use a tablet (such as an iPad) or a smart phone with an eye tracker. The eye tracker can be replaced by the integrated tablet/phone camera to serve as an eye tracker.

Figure 3:
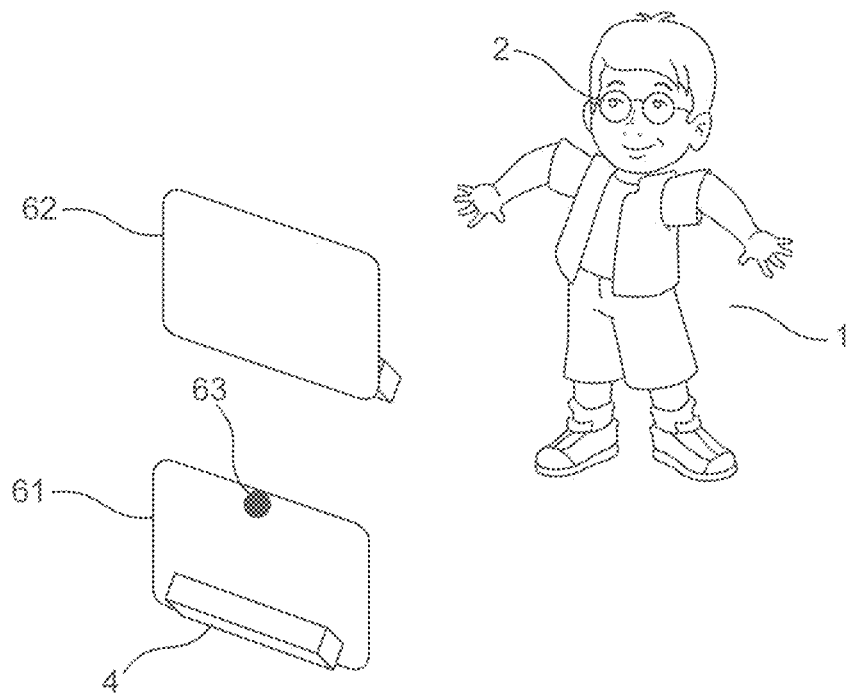
FIG. 3 shows a Portable apparatus, Tablet Based—a General View.

FIG. 3 shows a Portable Apparatus, Tablet Based. The apparatus includes 3D glasses 2, A tablet with a front view 61 and rear view 62, integrated camera 63 and remote eye tracker 4. Also shown is a patient 1.

Portable Apparatus with Goggles

Figure 4:
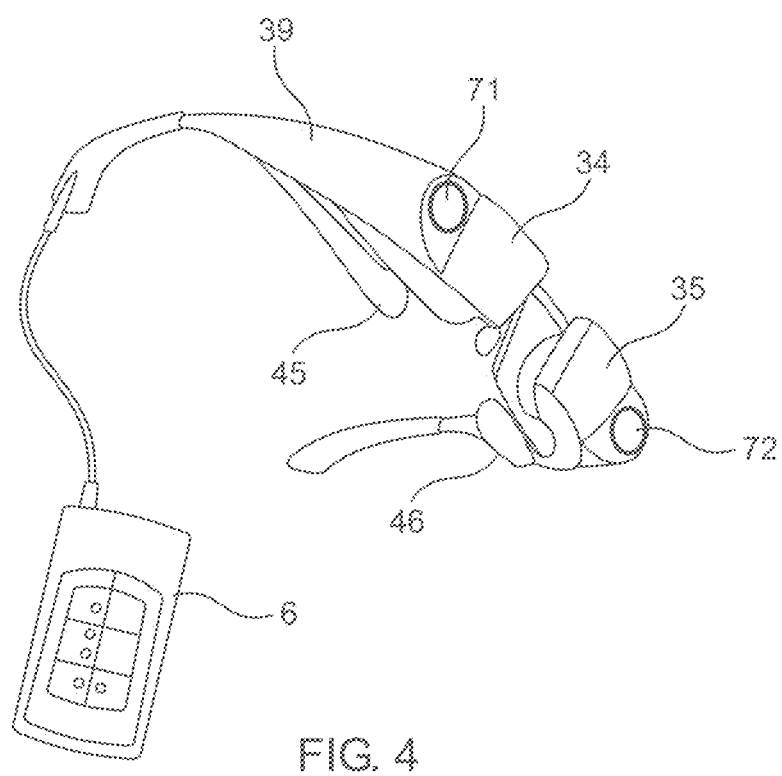
FIG. 4 shows a Portable Binocular apparatus—a General View.

The goggles embodiment comprises the following parts, see FIG. 4:
 Two eye trackers, one for each eye, located near the eyes; the right eye near tracker 45 and left eye near tracker 46.
 One or more micro-displays (with appropriate optics), one for each eye (in case of 2 micro displays), located near the eyes (this embodiment does not require a 3D display and 3D glasses); these are the right near eye display 34 and left near eye display 35.

The goggles might employ one or two scene cameras 71, 72 in case the apparatus will be used also during normal operation "on the go"

Ocular optics

Portable control box/processor 6.

The above detailed parts (possibly with the exclusion of the processor 6) may be mounted on a portable binocular or monocular frame 39

Figure 5:
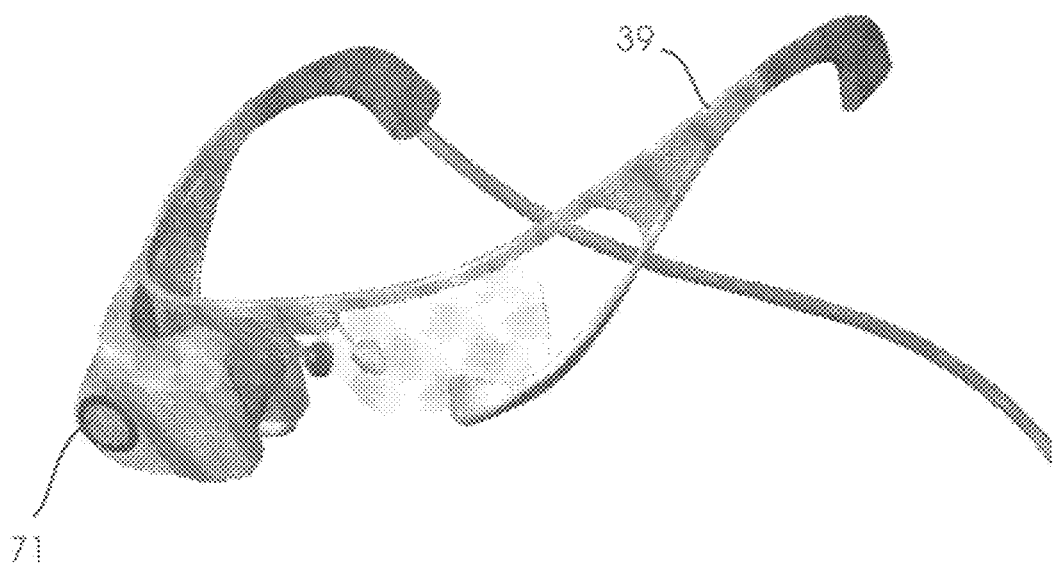
FIG. 5 shows a Portable Monocular Apparatus—a General View.
Figure 6A:
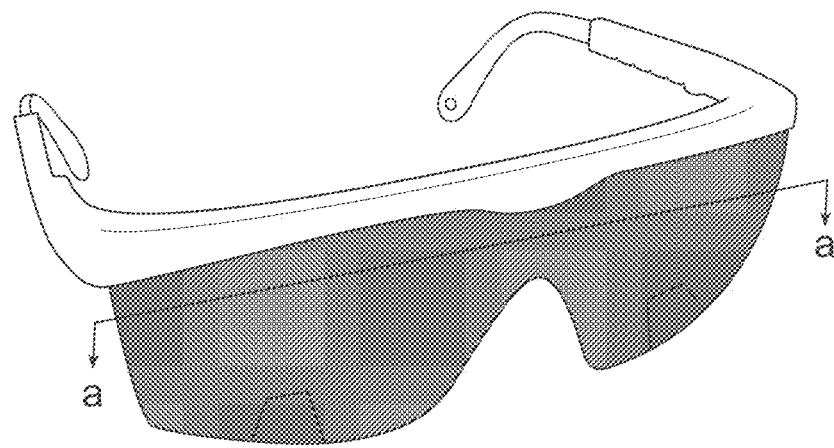
FIGS. 6A-6D shows a Portable Apparatus, Goggles Cross Sectional view.
Figure 6B:
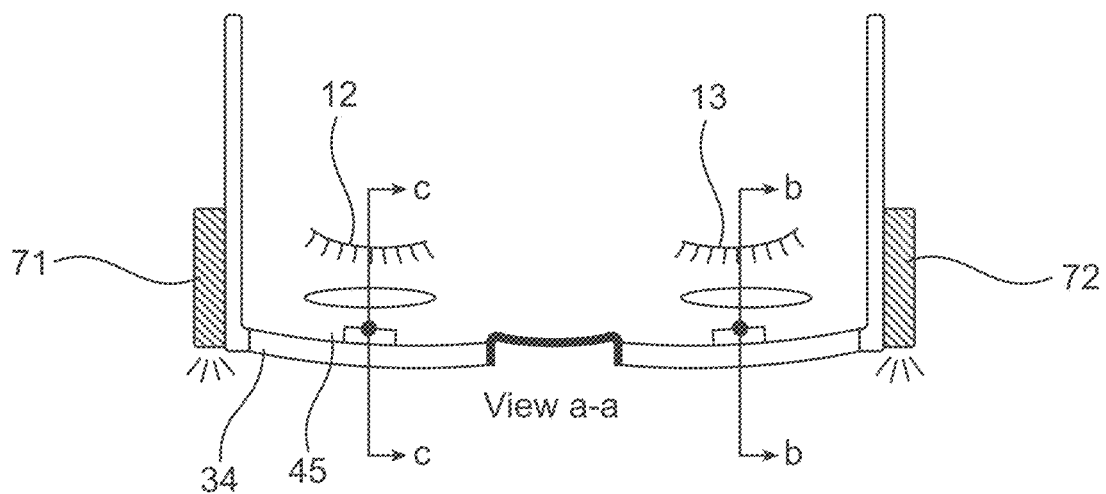
Figure 6C:
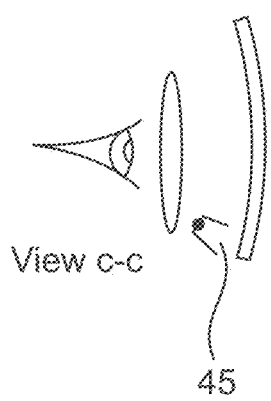
Figure 6D:
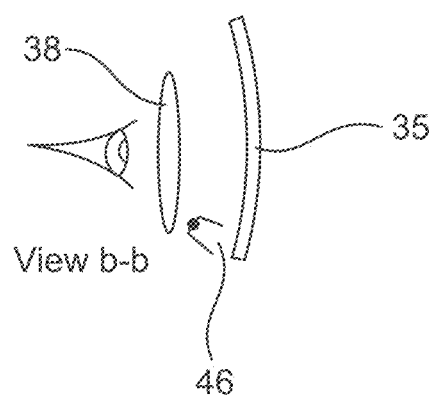

A monocular apparatus includes one micro display, one scene camera and one ocular optics, see FIG. 5. Shown are the portable binocular or monocular frame 39 and right scene camera 71.

FIGS. 6A-6D depict a cross-section of the goggles. The eye trackers 45, 46 are located below the eyes to eliminate obstruction of the image. The ocular lens 38 allows the eyes to focus on the micro-displays 34, 35 in order to project the image at the required distance according to the prescribed training program.

The ocular sub-assembly may include corrective optics if required by the patient.

The apparatus includes right scene camera 71, left scene camera 72, right near eye display 34, left near eye display 35, right eye near tracker 45, left eye near tracker 46 and eyepiece lens 38. Also shown are patient's right eye 12 and left eye 13.

Figure 7:
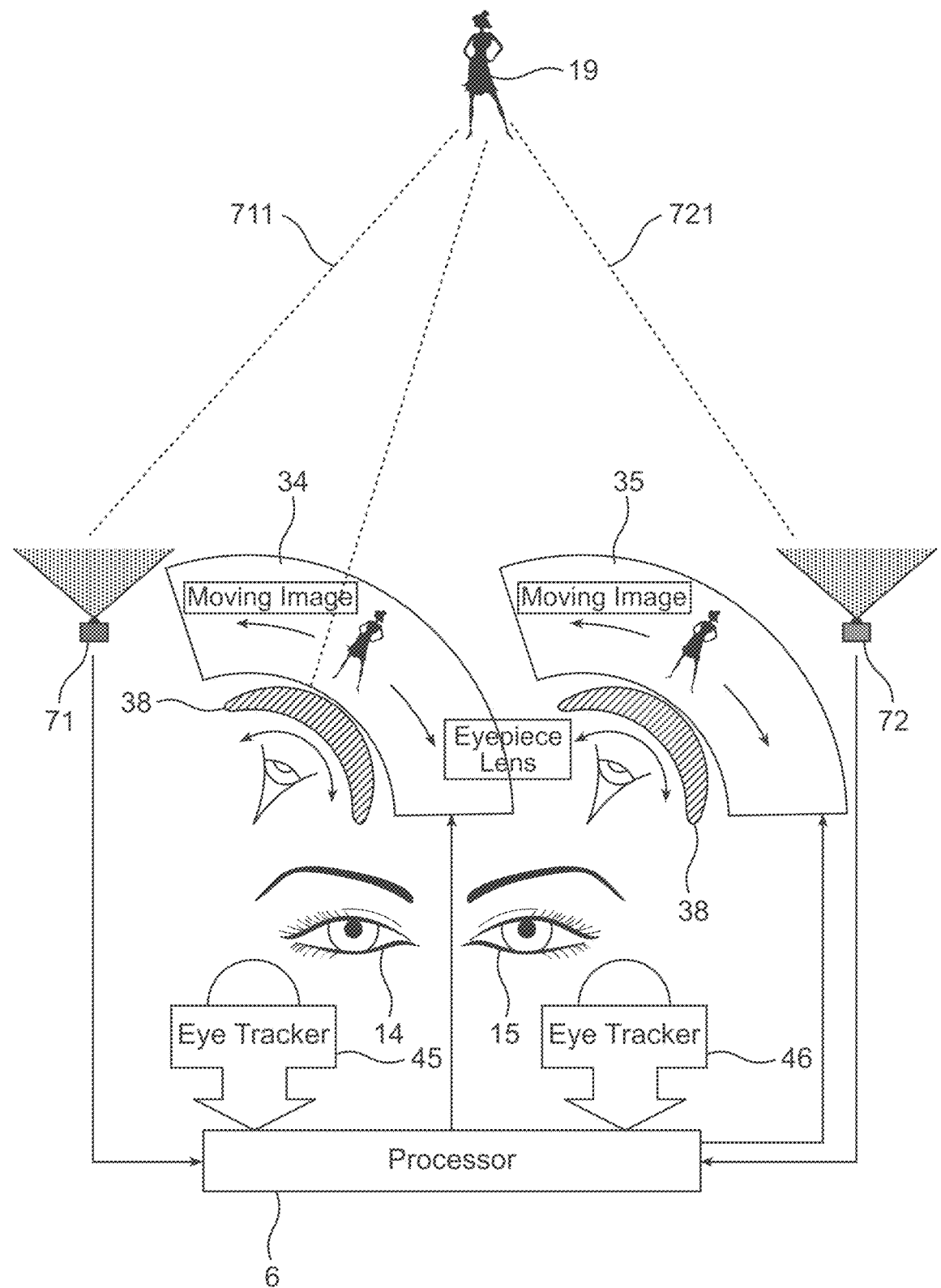
FIG. 7 shows a Portable Apparatus, Binocular, a Block Diagram.
Figure 8:
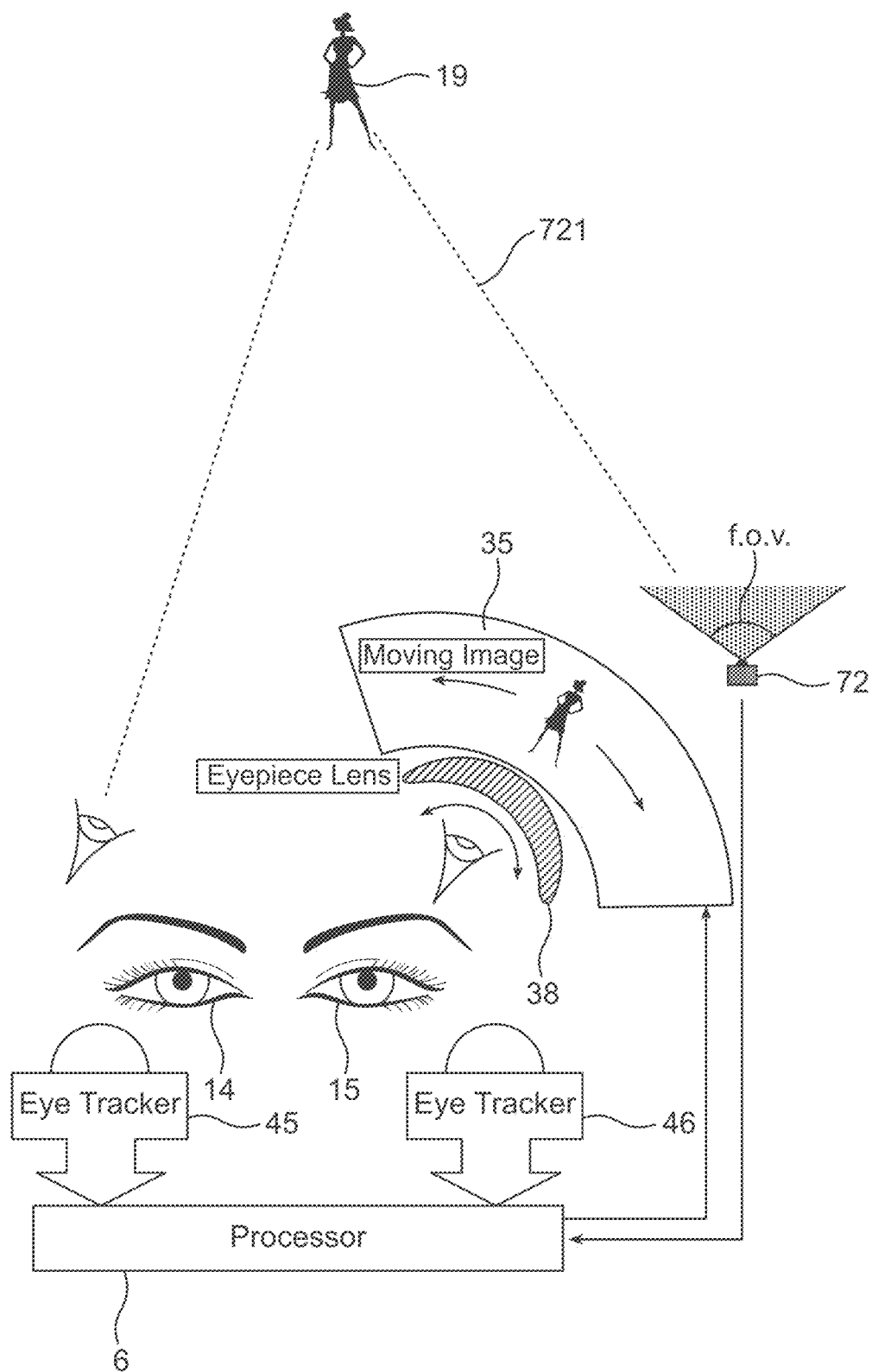
FIG. 8 shows a Portable Apparatus, Monocular, a Block Diagram.

The processor sends the required two dichoptic images (either stationary pictures, video, games, etc.) to the micro-displays—see a block diagram for binocular apparatus in FIG. 7 and a monocular apparatus FIG. 8.

The Control Box/Processor is not shown on these figures. In addition, the processor receives the eyes' gazing direction from the eye trackers and all required controls from the input devices such as the keyboard or control buttons on the goggles etc.

If required, the scene cameras capture the scene in front of the patient, processed accordingly by the processor to be displayed on the micro displays.

FIG. 7 shows a Portable Apparatus, Binocular, a Block Diagram including: eyepiece lens 38, near eye displays 34, 35, eye near trackers 45, 46, and scene cameras 71, 72. Also shown are patient's amblyopic eye 14 and nonamblyopic eye 15, an object or scenery 19, and virtual views 711, 721 from cameras to object.

FIG. 8 shows a Portable Apparatus, Monocular, a Block Diagram including: eyepiece lens 38, near eye display 35, eye near tracker 45, eye near tracker 46 and scene camera 72. Also shown are patient's amblyopic eye 14 and nonamblyopic eye 15, an object or scenery 19, and virtual view 721 from camera to object.

Principles of Operation

Principles of Operation for Amblyopia Treatment

The main requirement for amblyopia treatment is to prevent the amblyopic eye/brain apparatus from deterioration causing a permanent & incurable vision decrement. This must be accompanied (not the subject of the present invention) and in parallel, by addressing the cause for amblyopia. The processes enforce the brain to use the amblyopic eye.

In our apparatus, we enforce the brain to use the amblyopic eye but we do provide appropriate stimulation for the non-amblyopic eye as well, in order to train the stereopsis process and preserve the binocular vision and depth perception.

In order to overcome the problems of existing treatment options as mentioned above, our apparatus will work as follows:

The professional (ophthalmologist or optometrist) will determine the required type of stimulation. It can be either stationary pictures, video, games, normal scenery etc. Following are few examples:

Stimulating only the amblyopic eye for a certain percentage of time. The fellow eye does not receive any stimulation Stimulating the amblyopic eye with a clear and sharp image while providing the fellow eye with a blur image either by degeneration of sharpness, intensity, details etc.

Providing different segments of the image to each eye separately

Providing different locations of the right/left images in order to compensate for Strabismus in case of strabismic amblyopia The images might be provided separately for both eyes in such accommodation/convergence properties as required for creating virtual near or far image. The principle of operation is as described in our international patent application No. PCT/IL2016/050232.

The eyes tracker ensures that the stimulation center remains on the fovea region no matter in which direction each eye is looking at.

The method will provide treatment while the child is playing PC games, watching video etc.

Principles of Operation for Convergence Deficiency Diagnosis & Treatment and Heterophoria Treatment The main requirement for convergence deficiency diagnosis is to provide variable convergent images, beginning with relatively apart images which does not require the eyes to converge and gradually moving in the 2 images until the eye trackers will inform the processor that the eyes stopped converging.

The main requirement for convergence deficiency treatment is to provide variable convergent images, beginning with relatively apart images which does not require the eyes to converge and gradually moving in the 2 images to train them to converge.

In order to overcome the problems of existing treatment options as mentioned above, our apparatus will work as follows:

The professional (ophthalmologist or optometrist) will determine the required type of stimulation. It can be either stationary pictures, video, games, normal scenery etc. Following are few examples:

The images will be provided separately for both eyes in such convergence properties as required for creating virtual near or far image. The principle of operation is as described in our international patent application No. PCT/IL2016/050232, hereby included by reference.

The eyes tracker ensures that the stimulation center remains on the fovea region no matter to which direction each eye is looking at.

The same treatment can be performed for patient suffering from heterophoria.

Main Processes/Methods

Amblyopia Treatment

The process implemented in the various embodiments are similar. The description hereinafter is united and the differences are mentioned.

Figure 9:
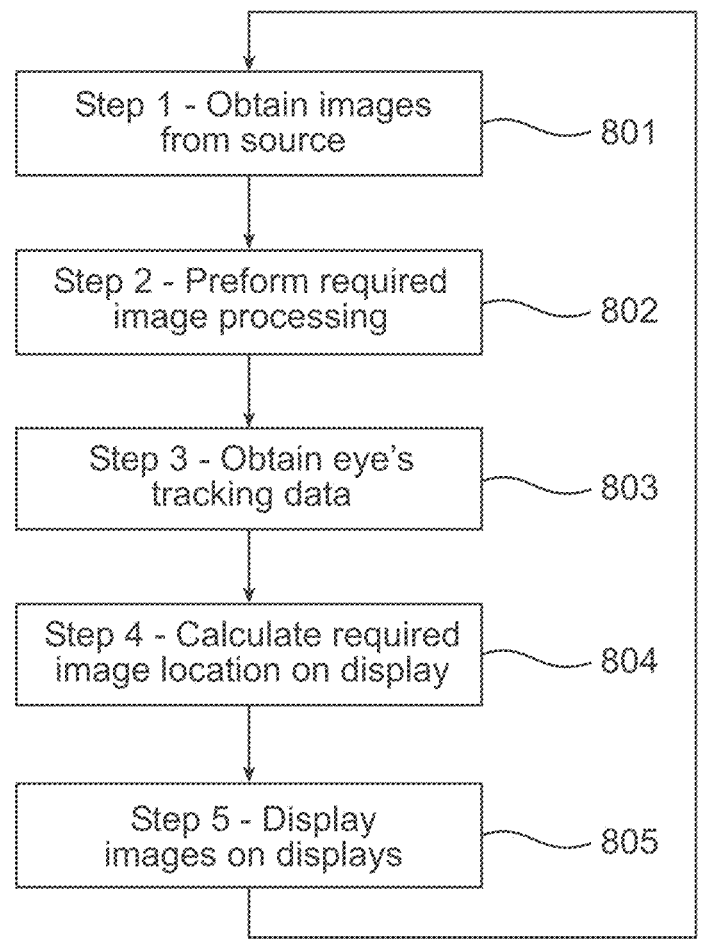
FIG. 9 shows a Method: Amblyopia Treatment Main Process.

FIG. 9 is the flowchart showing the basic process of treatment, including:

Step #1

The processor obtains the required images from the training program. The image source can be either stationary pictures, video, games, normal scenery etc. 801

Step #2

Figure 10A:
FIG. 10A shows the high contrast image presented to the amblyopic eye.
Figure 10B:
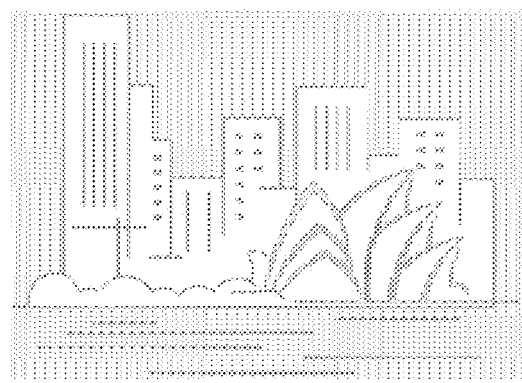
FIG. 10B shows the low contrast image presented to the fellow (better, stronger vision) eye.

The processor performs required image processing on the images. Following are some examples (There can be many more ways) 802:

- High contrast for amblyopic eye and low contrast for fellow eye (see FIGS. 10A, 10B). The contrast differences can vary with time (duty cycle), pictures quality, colors etc. This will encourage the brain to prefer to get more information from the amblyopic eye.

FIG. 10A shows the high contrast image presented to the amblyopic eye, and FIG. 10B shows the low contrast image presented to the fellow (better, stronger vision) eye.

Figure 11A:
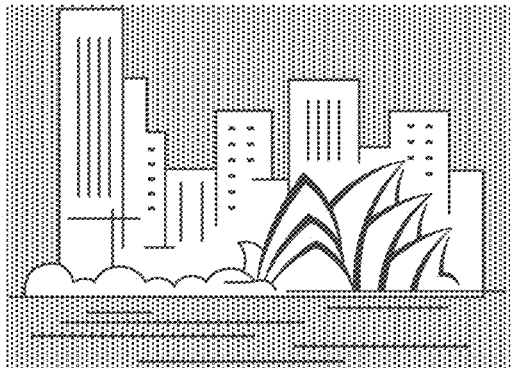
FIG. 11A shows the high contrast image presented to the amblyopic eye.
Figure 11B:
FIG. 11B shows the "no image" presented to the fellow (better, stronger vision) eye.

- No image for the fellow eye (see FIGS. 11A, 11B). The absence of image can vary with time (various duty cycles). This method is actually comparable to the existing eye patching method used currently.

FIG. 11A shows the high contrast image presented to the amblyopic eye, and FIG. 11B shows the "no image" presented to the fellow (better, stronger vision) eye.

Figure 12A:
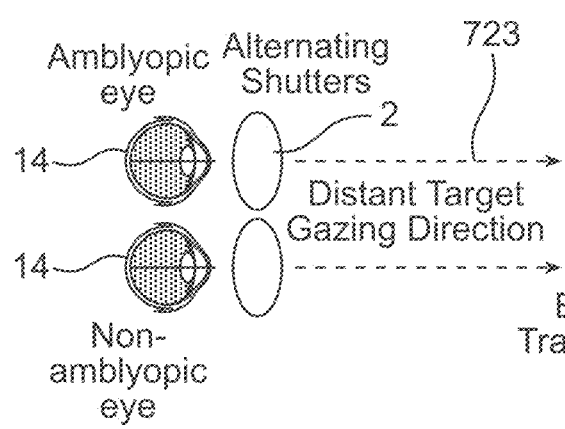
FIG. 12A shows the method of operation of the test or treatment.
Figure 12B:
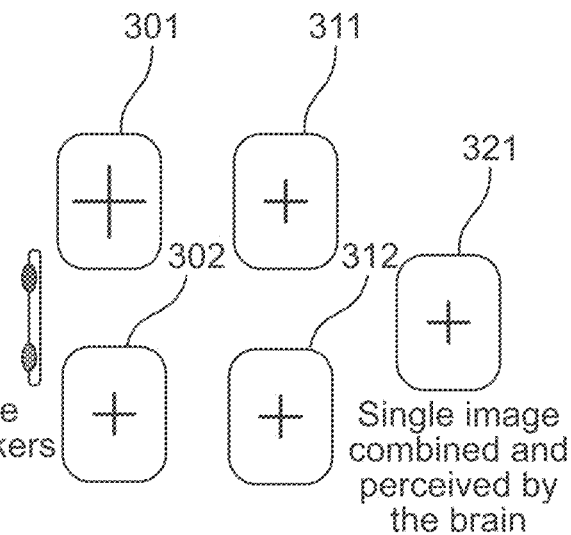
FIG. 12B shows the different sized images which would be presented on each eye's retina without an external intervention/correction.
Figure 12C:
FIGS. 12C, 12D show the different sized images which would be presented on each eye's retina without an external intervention/correction.
Figure 12D:
Figure 13A:
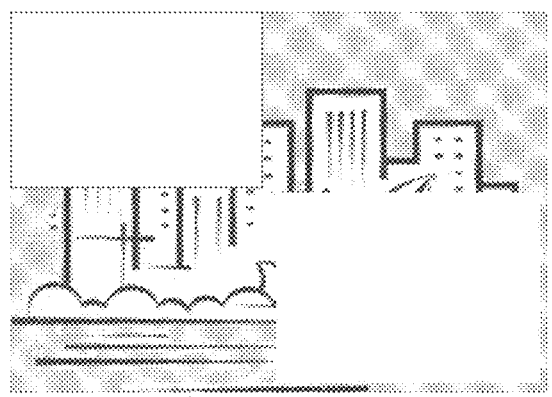
FIGS. 13A, 13B show a treatment method using different blobs, of complementary images, presented to each eye.
Figure 13B:
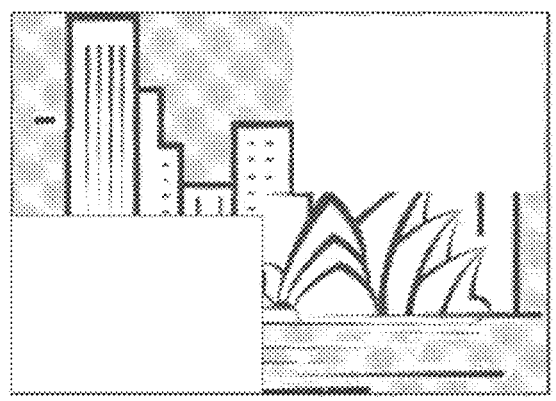

- Provide different sized images to each eye for cases of for treating anisometropic amblyopia in such a way that the 2 images will be perceived by the patient as identical size thus being able to be combined (see FIGS. 12A-12D) by the brain.
- Apply different complementary blobs of image to each eye (see FIGS. 13A, 13B). The blobs can be of different shapes and these shapes can also vary with time. This will enforce the brain to use the 2 eyes in order to perceive the whole details of the picture.

FIGS. 13A, 13B show a treatment method using different blobs, of complementary images, presented to each eye.

Figure 14A:
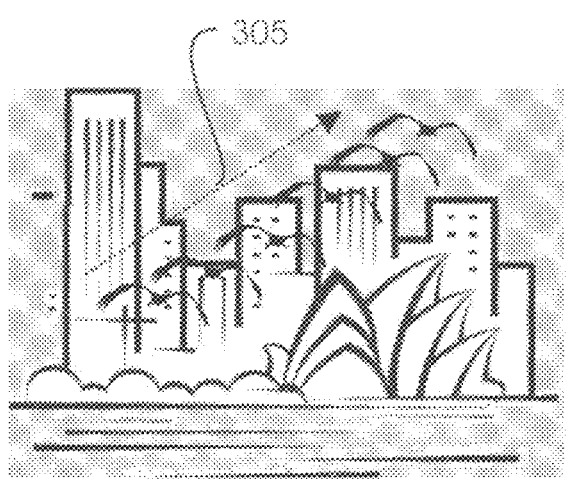
FIG. 14A shows a method of treatment using a moving object and FIG. 14B shows the image presented to the nonamblyopic eye, which does not include a moving object.

- Apply moving objects only (or mainly) to amblyopic eye (see FIG. 14A, which includes a flying bird 305). The moving object 305 can vary with time (duty cycle), speed, pictures quality, colors etc. This will challenge the brain to prefer the amblyopic eye.

Figure 14B:

FIG. 14A shows a method of treatment using a moving object 305 which is presented to the amblyopic eye, and FIG. 14B shows the image presented to the nonamblyopic eye, which does not include a moving object.

- Apply cognitive stimulations only (or mainly) to amblyopic eye. Such stimulations could be, for instance, targets of a computer game only for the amblyopic eye.

Any combinations of the above examples can be used in training.

The various parameters of every example could be changed and adjusted for the patient.

In all above, the training should be designed carefully, taking care that suppressing the good eye will not cause it to become amblyopic (reverse amblyopia).

Step #3

The processor receives each eye gazing direction from the eye trackers. 803

Step #4

The processor calculates the location on the screens 804. If the 2 eyes of the patient are parallel, the 2 images for both eyes should be displayed exactly on the same location on the monitor. Each eye will perceive each identical & relevant part of the picture exactly on the fovea. The brain will combine these 2 images into one 3D image, see FIGS. 15A, 15B. For clarity, the images on the figures are shown as a simple cross to emphasize the algorithm. The images can be parallel to simulate a far view as shown in FIGS. 15A, 15B or can be shifted inwards to simulate near view as shown in FIGS. 16A, 16B.

Figures 17A, 17B:
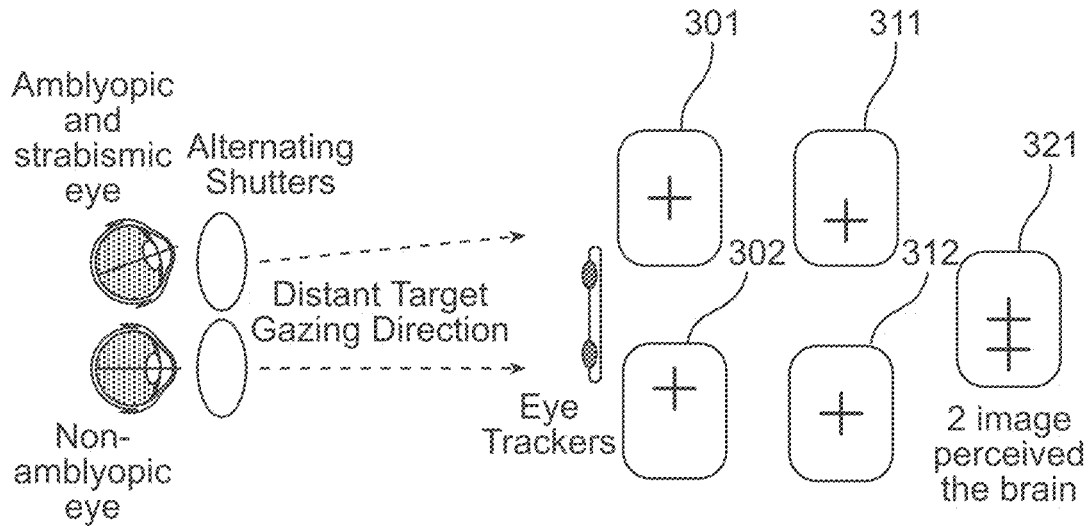
FIGS. 17A, 17B show Strabismic Eyes, Far Vision, Image Location Not Corrected.

Let's assume now that the 2 eyes of the patient are not parallel, e.g. the patient suffer from strabismus. If we display the images in parallel, as shown in FIGS. 17A, 17B, and as done with existing solutions, the non-strabismic eye will see the interest location of the image exactly on the fovea while the strabismic eye will see the interest location of the image on the right side of the fovea. The total perceived image will be diplopic (double vision) or the image of the strabismic eye will be ignored by the brain of the patient.

Our device will determine the relative gazing direction of each eye. Let's assume again that the 2 eyes of the patient are not parallel, e.g. the patient suffers from strabismus. We shift the image for the strabismic eye in such a way that its interest area will be projected exactly on the fovea. The non strabismic eye will also see the interest location of the image exactly on the fovea. The total perceived image will be combined by the brain and produce a single, normal 3D image, see FIGS. 18A, 18B.

Since we use eye trackers, the apparatus will compensate for any type of eyes' deviation, either concomitant (non-paralytic) or incomitant (paralytic) strabismus.

For strabismic eyes, a similar process will be applied in similar way for near sight training as explained above.

Step #5

The processor will display the 2 processed images on the proper location on the display and the process will continue during the whole training session. 805

FIG. 12A shows the method of operation of the test or treatment, with the amblyopic eye 14, nonamblyopic eye 15, 3D glasses 2, and the distant target gazing direction 723.

FIG. 12B shows the different sized images 301, 302 which would be presented on each eye's retina without an external intervention/correction. This effect is due to a patient's vision problem (a difference in eyes magnification, or zoom). Such different sized images may prevent the images to be combined in the brain. One goal of our invention is to correct the image presented to one eye, by enlarging or reducing the image as required, to obtain the same sized images 311, 312 in both eyes. The same size images will be combined in the brain into one image 321 (a tri-dimensional image if the original images 301, 302 pertain in a 3D object). FIGS. 12C, 12D show the different sized images which would be presented on each eye's retina without an external intervention/correction.

FIG. 14A shows a method of treatment using a moving object 305 which is presented to the amblyopic eye, and FIG. 14B shows the image presented to the nonamblyopic eye, which does not include a moving object.

FIGS. 15A, 15B show non strabismic eyes, far vision.

FIG. 15B shows the images 301, 302 which would be presented on each eye's retina without an external intervention/correction. The images are correctly of the same size and appear at the same location on the retina, thus correction is not required.

FIGS. 16A, 16B show non strabismic eyes, near vision.

FIG. 16B shows the images 301, 302 which would be presented on each eye's retina without an external intervention/correction. The images are not presented on the same location for both eyes, therefore there is a problem in combining them in the brain.

One goal of our invention is to correct the images presented to one eye or both eyes, by changing the location of the images presented on the retina, so identical or similar images appear on the same location as shown with corrected images 311, 312 in both eyes. The same size images will be correctly combined in the brain into one image 321 (a tri-dimensional image if the original images 301, 302 pertain in a 3D object).

FIGS. 17A, 17B show Strabismic Eyes, Far Vision, Image Location Not Corrected.

FIG. 17B shows the images 301, 302 which would be presented on each eye's retina without an external intervention/correction. The images would be presented on the same location for both eyes, but the eyes point in different directions, therefore the perceived images 311, 312 are not co-located, and there is a problem in combining them in the brain, as shown in image 321.

Figures 18A, 18B:
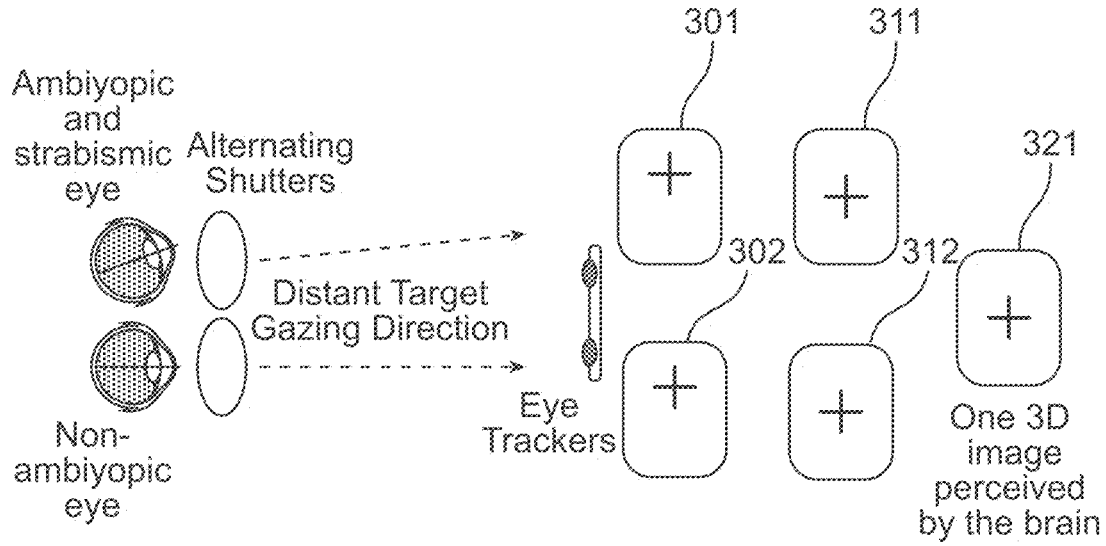
FIGS. 18A, 18B show Strabismic Eyes, Far Vision, Corrected Image Location.

FIGS. 18A, 18B show Strabismic Eyes, Far Vision, Corrected Image Location.

One goal of our invention is to correct the images presented to one eye or both eyes, by changing the location of the images presented on the retina 301 and 302, so identical or similar images appear on the same location as shown with corrected images 311, 312 in both eyes. The same size images will be correctly combined in the brain into one image 321 (a tri-dimensional image if the original images 301, 302 pertain in a 3D object).

Convergence Insufficiency Diagnosis

The processes implemented in the various embodiments are similar. The description hereinafter is united and the differences are mentioned, if exist.

Figure 19:
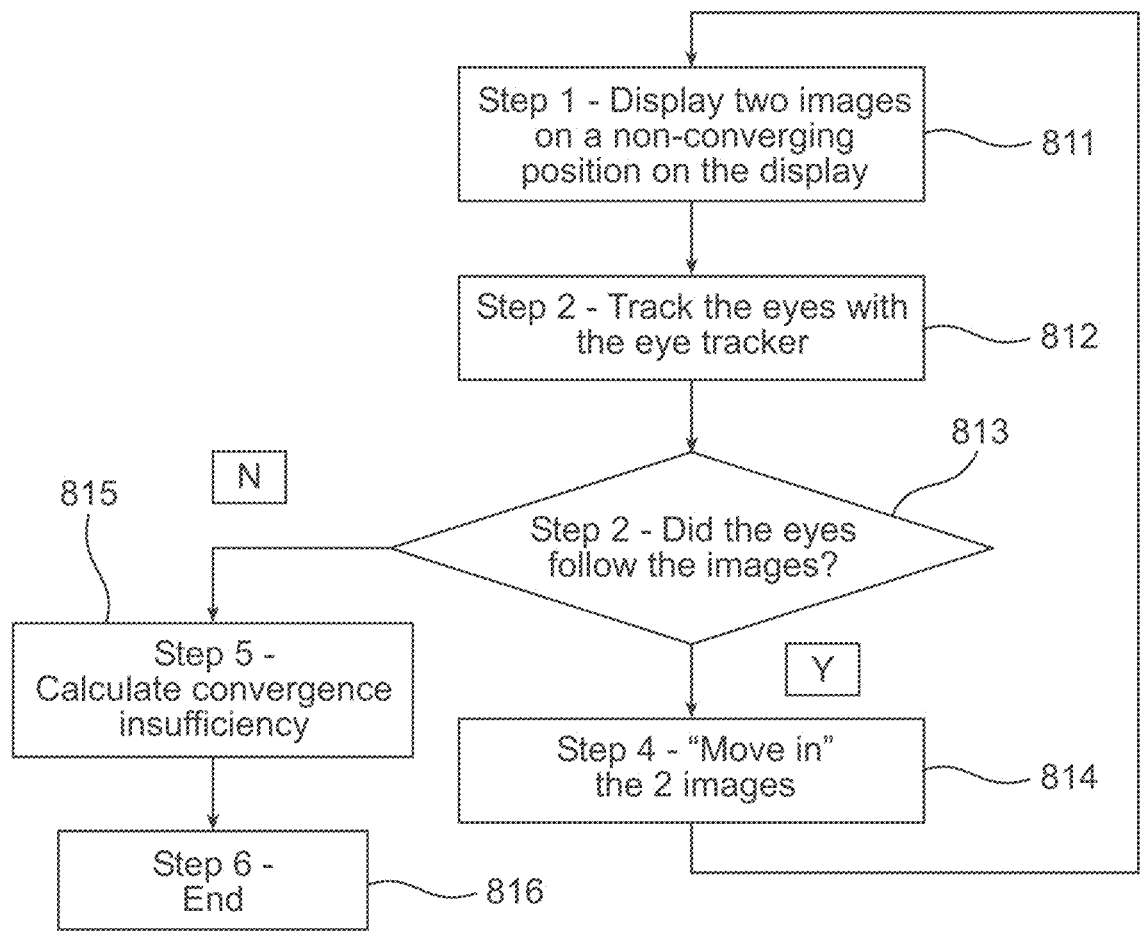
FIG. 19 shows a Method for convergence insufficiency diagnosis, main process.

FIG. 19 is the flowchart showing the basic process of diagnosis, comprising:

Step #1

The processor obtains the required images from the training program and display them on the display in the initial, non-converging locations. The image source can be either stationary pictures, video, games, normal scenery etc. See FIG. 20. The 2 eyes are parallel as in the case the image is far away. 811

Step #2

The eye trackers track the eyes and inform the processor whether the eyes tracked the image. 812

Step #3

If the eyes tracked the image, the process will go to step 4. If the eyes did not track the image, the process will go to step 5. 813

Step #4

The images will "move in", for example by additional 1 degree. 814. See also FIGS. 21A, 21B.

Step #5

Figures 22A, 22B:
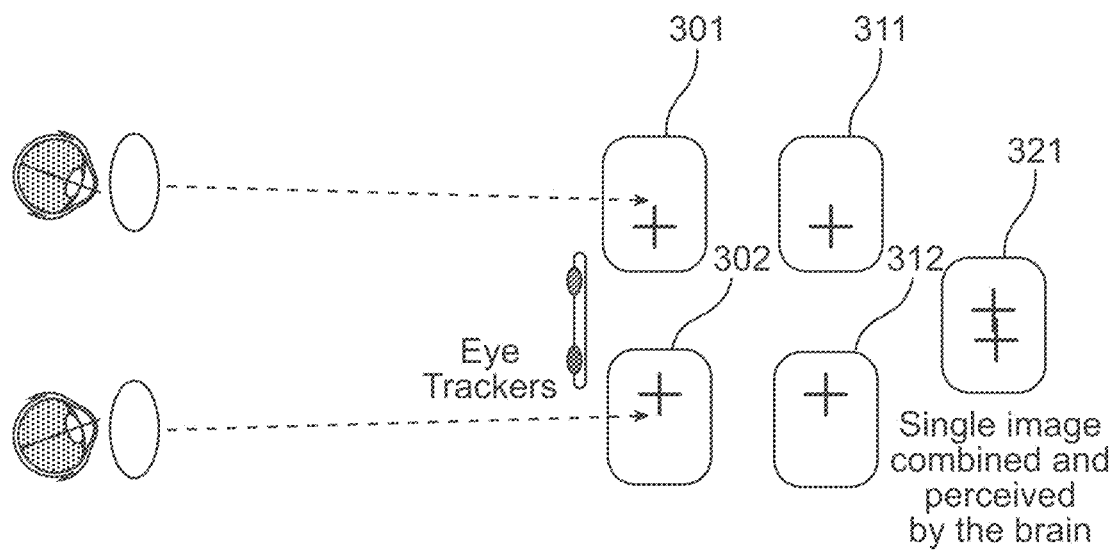
FIGS. 22A, 22B show Image Location—Insufficient-Converging Eyes.

If the eyes did not track the images, the perceived images will be as seen in FIGS. 22A, 22B.

The processor will calculate the convergence insufficiency angle according to the last angle. If the eyes converged at least as the required convergence for the specific target distance then convergence insufficiency could be ruled out. 815

Step #6

End of process, the process might be repeated a few times in order to average and get more accurate results. 816

Figures 20A, 20B:
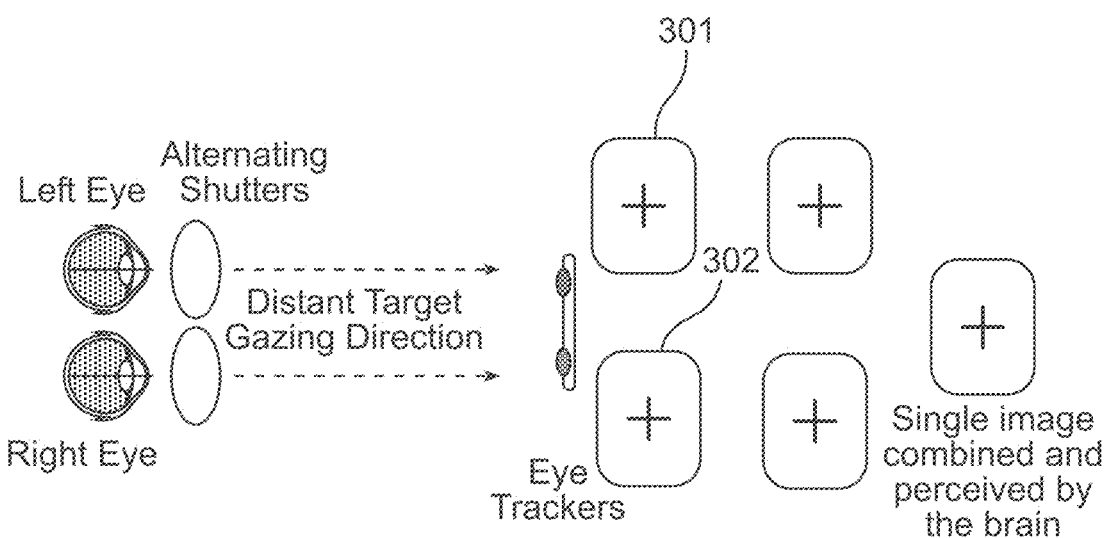
FIGS. 20A, 20B show Initial Image Location—Far Vision.

FIGS. 20A, 20B show Initial Image Location—Far Vision.

FIG. 20B shows the images 301, 302 which would be presented on each eye's retina without an external intervention/correction. The images are correctly of the same size and appear at the same location on the retina, thus correction is not required.

Figures 21A, 21B:
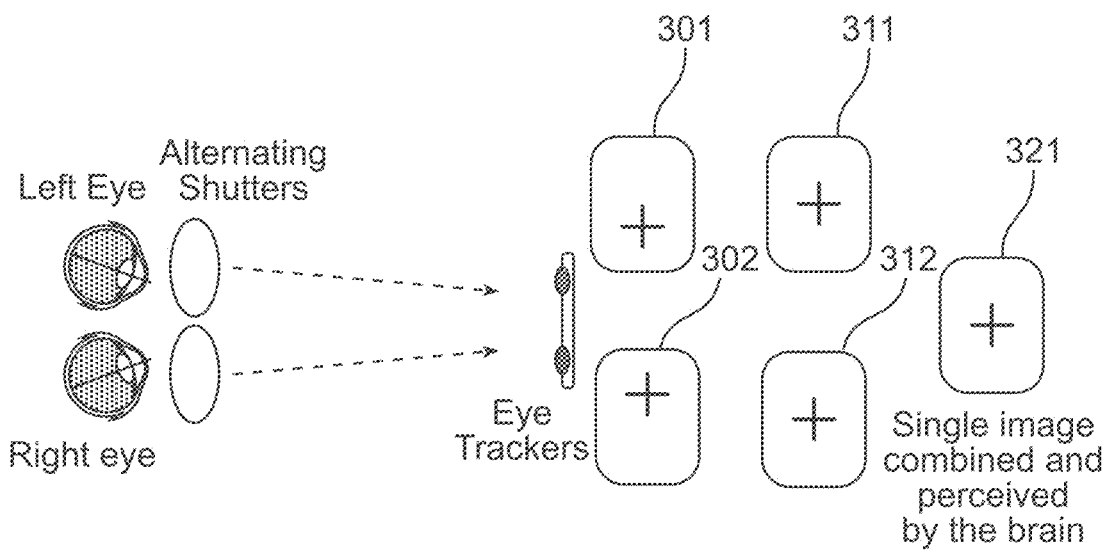
FIGS. 21A, 21B show Image Location—After "moving in".

FIGS. 21A, 21B show Image Location—After "moving in".

One goal of our invention is to correct the images presented to one eye or both eyes, by changing the location of the images presented on the retina 301 and 302, so identical or similar images appear on the same location as shown with corrected images 311, 312 in both eyes. The same size images will be correctly combined in the brain into one image 321.

FIGS. 22A, 22B show Image Location—Insufficient-Converging Eyes.

FIG. 22B shows the images 301, 302 which would be presented on each eye's retina without an external intervention/correction. The images are not co-located, therefore the perceived images 311, 312 are not co-located, and there is a problem in combining them in the brain, as shown in image 321.

Convergence Insufficiency and Heterophoria Treatment

The treatment will be performed as detailed above with reference to "Convergence Insufficiency Diagnosis", with the following changes:

Once the convergence insufficiency will be determined, the addition of "moving in the image" will stop just before the eyes will lose the image tracking and the training will repeat according to the training program, for example, 15 minutes a day. The diagnosis process will be initiates occasionally and if a progress will be detected, an addition of 1 degree, for example, will be added to the images "move in" parameters.

In order to improve efficiency of the treatment, the exercise may be continued even beyond optimal convergence to achieve a better training for the child.

Monitoring and Assessment

The apparatus can measure, at regular intervals and during routine exercises, various parameters such as:
- Visual acuity
- Strabismus angle and extent of heterophoria
- Extent of stereopsis
- Color Blindness Test
- Convergence insufficiency diagnosis
- Eye movements: saccades speeds, trajectory and reaction time, vestibulo-ocular reflex measurements
- Optokinetic reflex measurements
- Reading speed
- Pupil testing Based upon the results, the apparatus will assess the progress of the patient and:
- Recommended changes in the treatment program
- Provide a feedback signal to the trainee
- Automatically change the treatment program.

Visual Acuity Test

Figure 24:
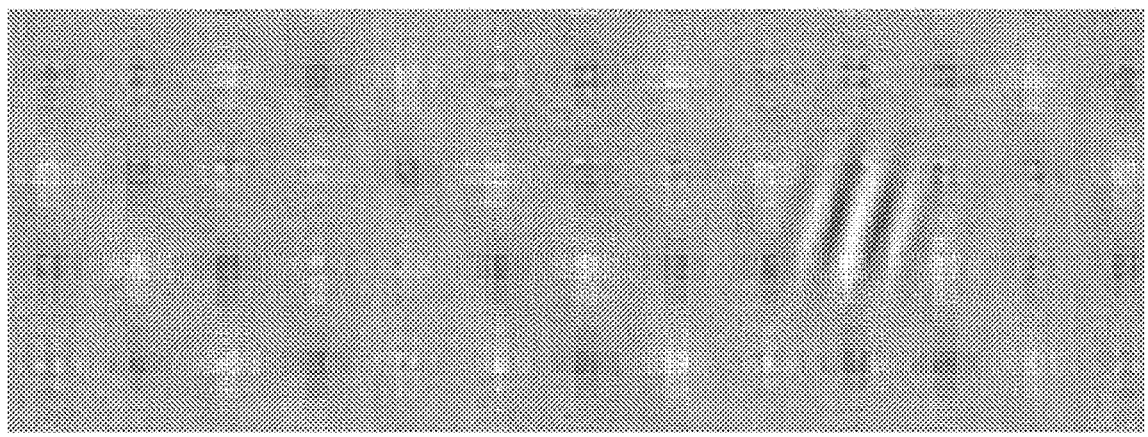
FIG. 24 illustrates a Typical Gabor Patch Image.

The automatic test can be performed in several ways. One example is explained in detail below. The test may be performed using "Gabor Patch" images, see FIG. 24.

The process is based on a technique called "Teller Acuity Cards" which is a known practice in ophthalmology to measure the visual acuity of small children.

Figure 25:
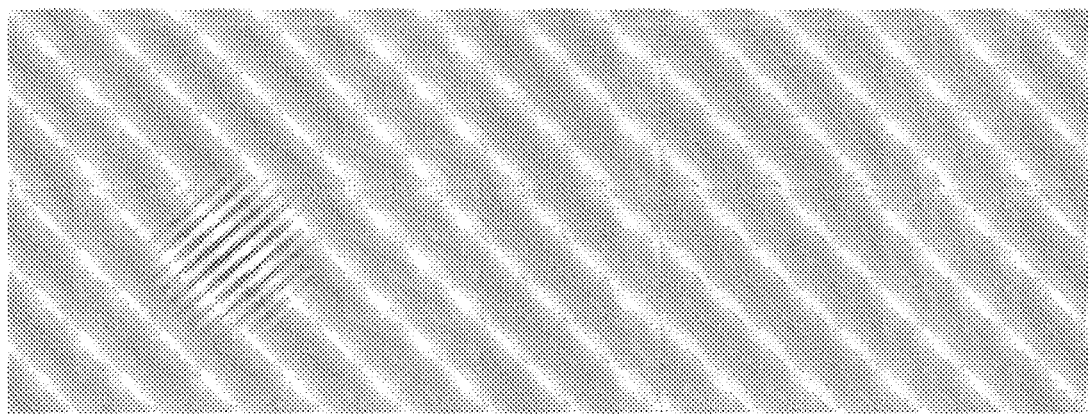
FIG. 25 illustrates a Gabor Patch with Higher Spatial Frequency.
Figure 26:
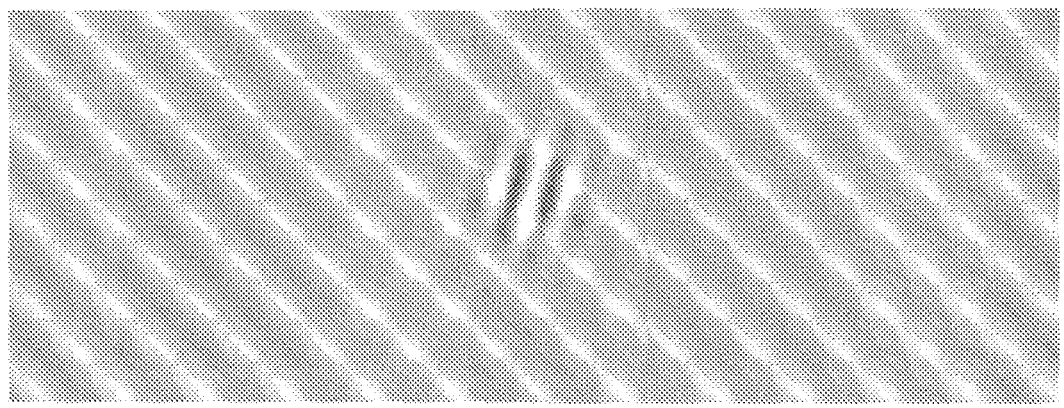
FIG. 26 illustrates a Rotated Gabor Patch.
Figure 27:
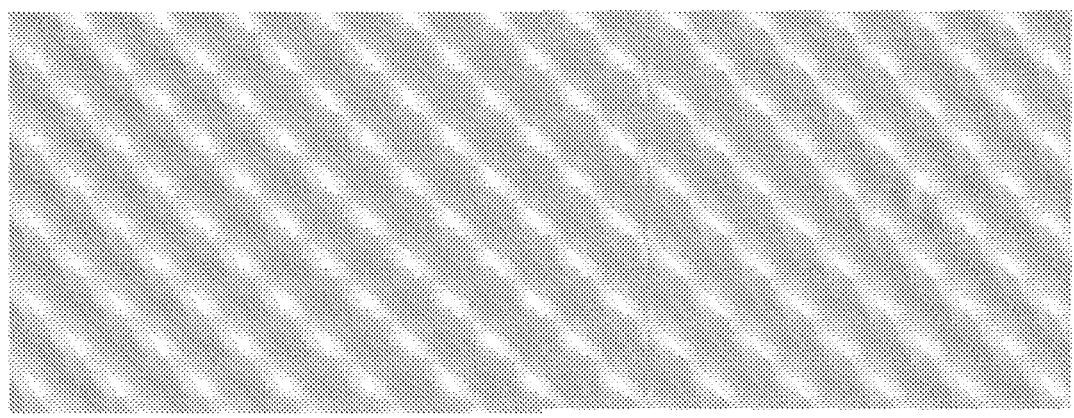
FIG. 27 illustrates a Gabor Patch with Reduced Contrast.

The Gabor Patch can be modified by various parameters. For example:
- Spatial frequency—changing the distance between adjacent lines—see FIG. 25
- Orientation—see FIG. 26
- Contrast—see FIG. 27
- Location and dynamic—the Gabor patch can be displayed on various screen locations and moving at different speeds.

Our apparatus performs the test automatically by changing the various parameters of the patch while tracking the eye and determining whether the eye tracks the patch or not. In addition, performing this test manually with cards is done statically—typically the pattern will be displayed either in the left side or right side of the visual field. Our apparatus provides the location dynamically in any area of the field of view.

We will present herein a test performed for a single eye. This process can similarly be performed for the second eye as well.

Since the test has to be performed to each eye separately, the non-tested eye has to be occluded. This can be done either by a mechanical occlusion as performed today in conventional visual acuity tests or by using 3D display and 3D glasses as described throughout this document. In the case of goggles portable embodiment, this will be performed by projecting the image only to the tested eye.

Figure 23:
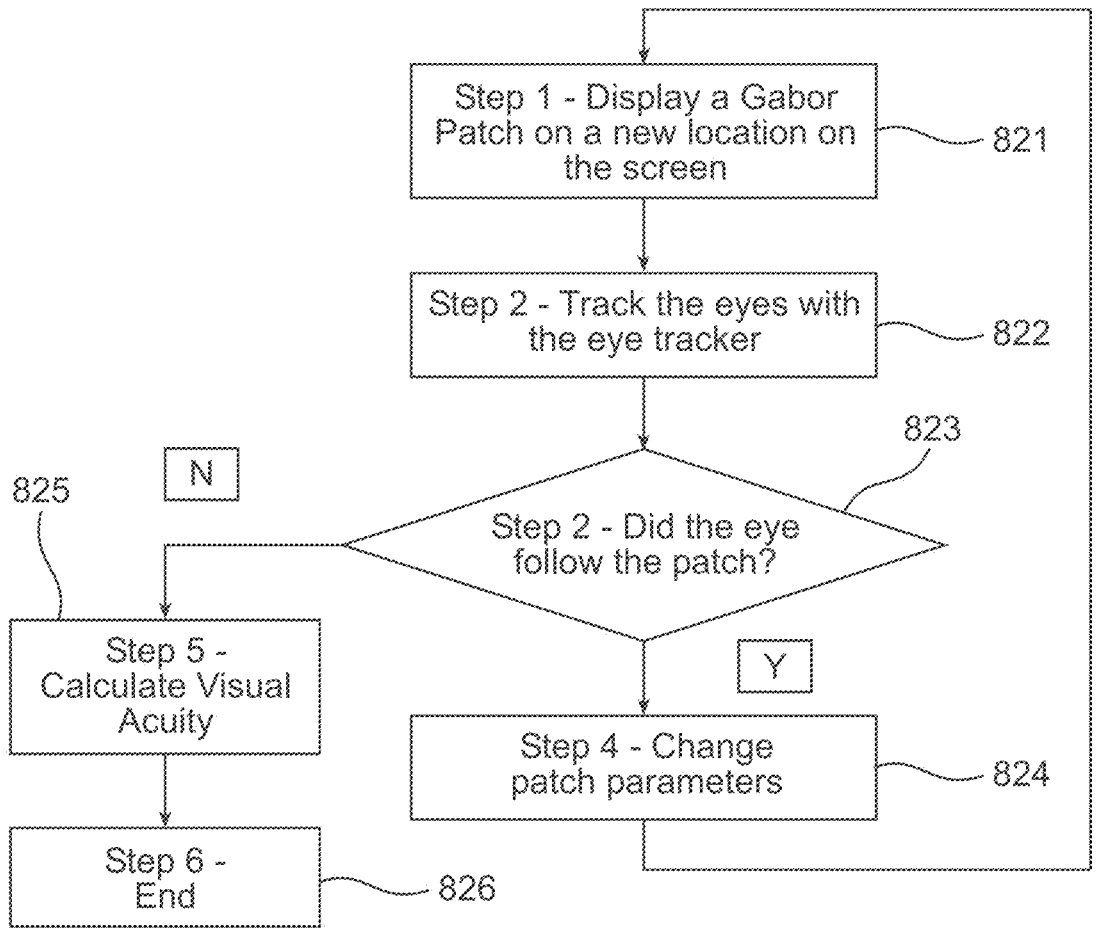
FIG. 23 shows a Method for Visual Acuity, Main Process.

FIG. 23 shows the visual acuity main process or method, including:

Step 1—The Gabor image (initially with low spatial frequency and high contrast) is moved to a location on the display. 821

Step 2—Track the eyes with the eye tracker and provide the data to the processor. 822

Step 3—The processor will determine whether the eye tracked the target. If the eye was tracking the Gabor Patch the process will move to step 4. If the eye will not be able to see and/or track the patch, the process will go to step 5. 823

Step 4—The patch parameters will become harder to track by increasing the spatial frequency (the bars become progressively finer or closer together), by decreasing the contrast, by increasing the patch movement speed and so on, provide a new location and go back to step 1. 824

Step 5—The processor will calculate the visual acuity based on the last tracked patch and standard existing tables that correlate that patch to the relevant visual acuity. 825

The test can be conducted with other images than the Gabor Patches by providing more attractive targets for children like animals, cartoon heroes, symbols etc.

The images can be stationary on different parts of the screens or moving in various speeds while the eye trackers determine whether the eyes follow the targets.

The image might be shown with different orientations and by checking the tracking ability of the different orientations, an information about possible astigmatism and the astigmatism axis might be gathered.

Step 6—End. 826

Strabismus and Heterophoria Test

The strabismus test is performed as described in our international patent application No. PCT/IL2016/050232, hereby included by reference.

Stereopsis Depth Test

Stereopsis is the process of perception of depth and 3-dimensional structure obtained on the basis of visual information derived from two eyes. Because the eyes of humans are located at different lateral positions on the head, binocular vision results in two slightly different images projected to the retinas of the eyes. The differences are mainly in the relative horizontal position of different objects in the two images. These positional differences are referred to as horizontal disparities. These disparities are processed in the visual cortex of the brain to yield depth perception.

While binocular disparities are naturally present when viewing a real 3-dimensional scene with two eyes, they can also be simulated by artificially presenting two different images separately to each eye. The perception of depth in such cases is also referred to as "stereoscopic depth".

A person perceives 3D impression not only by the horizontal disparities effect of binocular vision, but also by monocular clues such as relative objects size, relative motion and more.

Our automatic test can be performed in several ways. One example is explained in detail below.

Prior Art Method:

The test example shown here has no monocular clues thus provides a reliable assessment of stereo-acuity resulting from binocular disparity and stereopsis process performed in the visual cortex.

Figure 29:
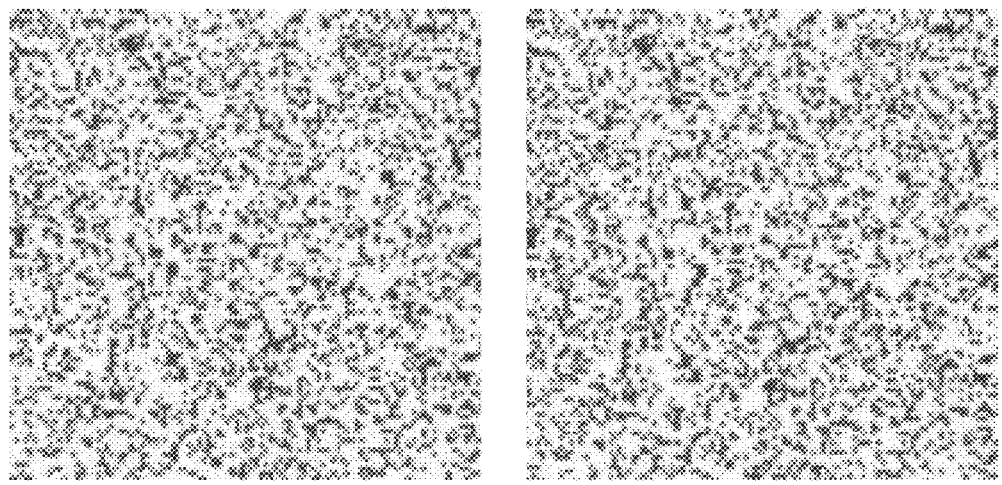
FIG. 29 shows a Typical Random Dot Stereogram.

The test is based on Random Dot Stereograms (RDS)—see FIG. 29. This technique is routinely used to assess the level of stereoscopic depth of a person. It has 2 images which are orthogonally polarized so that a person wearing eyeglasses with 2 orthogonally polarized filter will view each image with the appropriate eye.

A part of these 2 images is horizontally shifted so as to create the required spatial difference in such a way that when viewed by both eye separately, produces the perception of depth, with objects appearing to be in front of or behind the display level. See an example of a square as perceived by a person with normal depth perception—FIG. 30. The shifted region produces the binocular disparity necessary to give a sensation of depth. Different shifts correspond to different depths.

Figure 31:
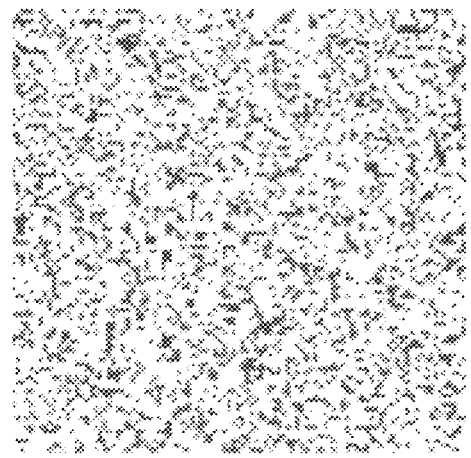
FIG. 31 shows the Image (random dots) Perceived by a Person with No depth perception.

A person with no depth perception, or a normal person looking with only a single eye, will see just randomly dots as depicted in FIG. 31.

The shapes can be of any kind—letters, geometrical, animals etc., in colors or black and white and so on.

The disparity of the relevant part in the images can vary, according to standard values used in current procedures, for example, from 4,800 to 12.5 seconds of arc. The lower the disparity recognized as being seen as 3D image by the tested person, the better his stereo-acuity.

Our Apparatus:

Our apparatus performs the test automatically by creating RDSs and moving the target image from side to side on predetermined paths and predefined speeds while the eye trackers determine whether the eyes follow the targets or not.

As the patient tracks appropriately the target, the horizontal disparity of the target image will gradually change from highest disparity to a lower disparity until the eye tracker will determine that there is no tracking any more. If the patient does not have depth perception, he will not be able to track the target.

Our method to display the 2 images to each eye separately is performed as explained throughout this document.

Figure 28:
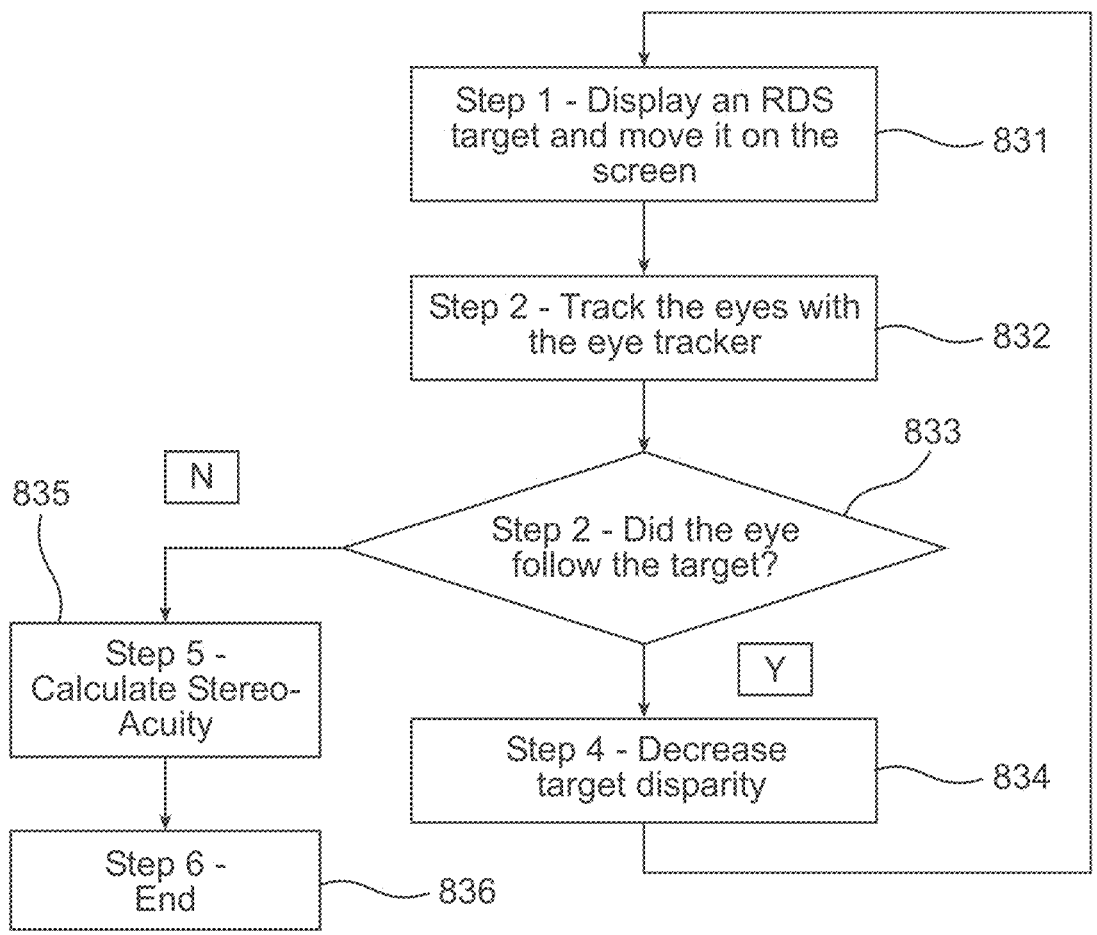
FIG. 28 shows a Method for Stereo Acuity Test, Main Process.

FIG. 28 shows the stereo acuity test main process. The method includes:

Step 1—Display an RDS target with high disparity (in initialization phase) and move it on the screen. 831

Step 2—Track the eyes with the eye tracker and provide the data to the processor. 832

Step 3—The processor will determine whether the eye see/tracked the target along its path. If the eye was tracking the 3D target the process will move to step 4. If the eye will not be able to see and/or track the target, the process will go to step 5. 833

Step 4—The target disparity parameters will decrease and go back to step 1. 834

Step 5—The processor will calculate the stereo-acuity based on the last tracked target disparity and standard existing tables that correlate that last disparity to the relevant stereo-acuity. 835

Figure 30:
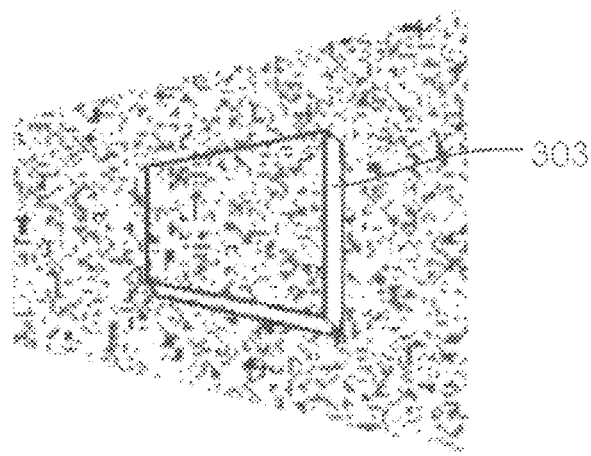
FIG. 30 shows a 3D Image as Perceived by a Normal Viewer.

Step 6—End. 836
The test can be conducted with other images than the geometric shapes by providing more attractive targets for children like animals, cartoon heroes, symbols etc.
FIG. 29 shows a Typical Random Dot Stereogram.
FIG. 30 shows a 3D Image 303 as Perceived by a Normal Viewer.
FIG. 31 shows the Image (random dots) Perceived by a Person with No depth perception.

Color Blindness Test

Color blindness affects about 8% of men and 0.5% of women.

Prior Art Method:

An example of the most popular test are the Ishihara plates. The test consists of 38 different pseudo isochromatic plates, each of them hides a number or shape behind colorful dots. Based on what you can see and what not, it is possible to check if you are suffering from some form of color blindness. The cooperation of the subject is needed for informing what number or shape he sees.

In the following picture we show an example of Ishihara plate. For practical reasons of patent drawings, we show the drawings only in gray scale. However, the color plates are very common and any one skilled in the art is aware of the real color plates.

Figure 32:
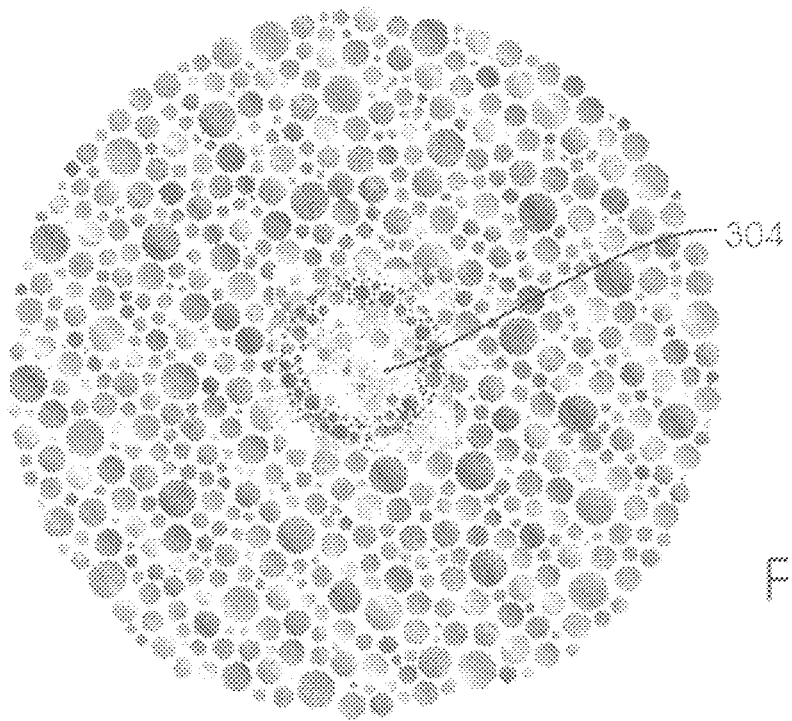
FIG. 32 shows the Image Perceived by a Normal Person.

FIG. 32 depicts, for example, a typical red/green Ishihara color blindness target. The various dots are colored in red and green colors in various intensities, contrasts and different sizes.

The depth of color perception can be tested by altering the various intensities, contrasts and different sizes.

Figure 33:
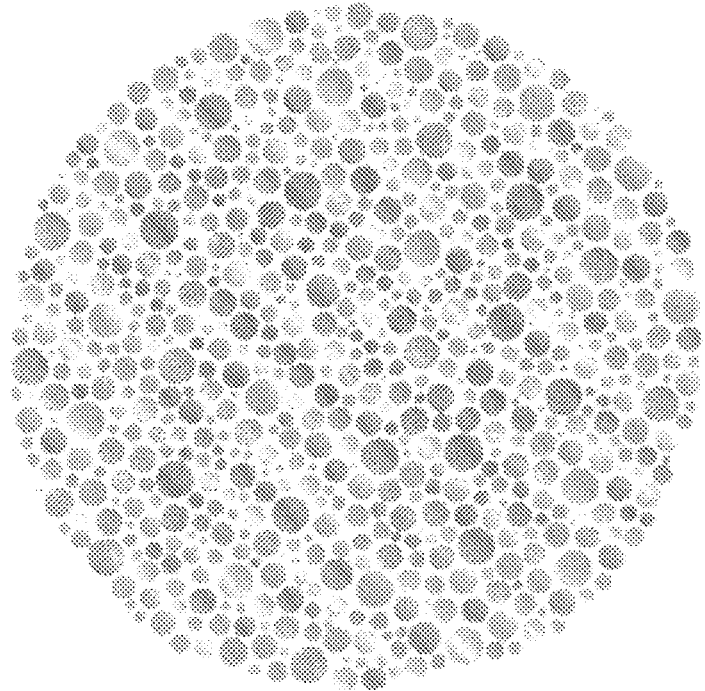
FIG. 33 shows the Image Perceived by a Color-Blind Person (no color ring is seen).

A normal person will see a color ring 304 as shown in FIG. 32. A red/green color blinded person will not see the circle but a collection of random dots in various intensities and different sizes as shown in FIG. 33 and will not be able to track the circle.

Figure 34:
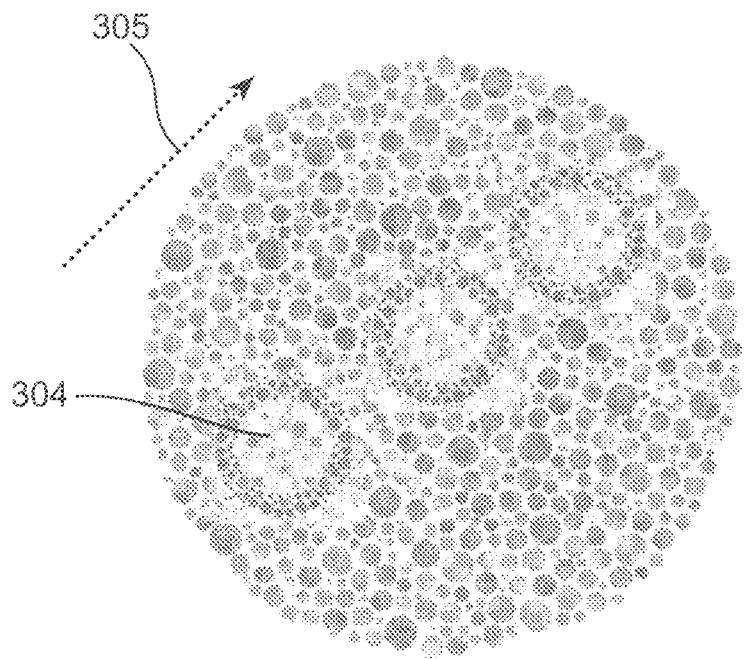
FIG. 34 shows the test method of Moving the Shape.

Our Apparatus:

Our new apparatus and method performs the test the color perception depth automatically. It will create a target shape that will attract the eyes (for example, for a small child a shape of a bear) and move the target image on the display at predetermined paths and speeds (See example in FIG. 34) while the eye trackers determine whether the eyes follow the targets. FIG. 34 shows the test method of Moving the Shape. The color ring 304 is shown in three consecutive locations, as it moves in the direction as indicated with the arrow 305

As the patient tracks appropriately the target, the intensity, contrast and size of the dots will gradually change from higher intensity, contrast and size to a lower intensity, contrast and size until the eye tracker will determine that there is no tracking any more.

The point where the person's eyes will stop tracking will be indicative of his/her color depth perception.

Figure 35:
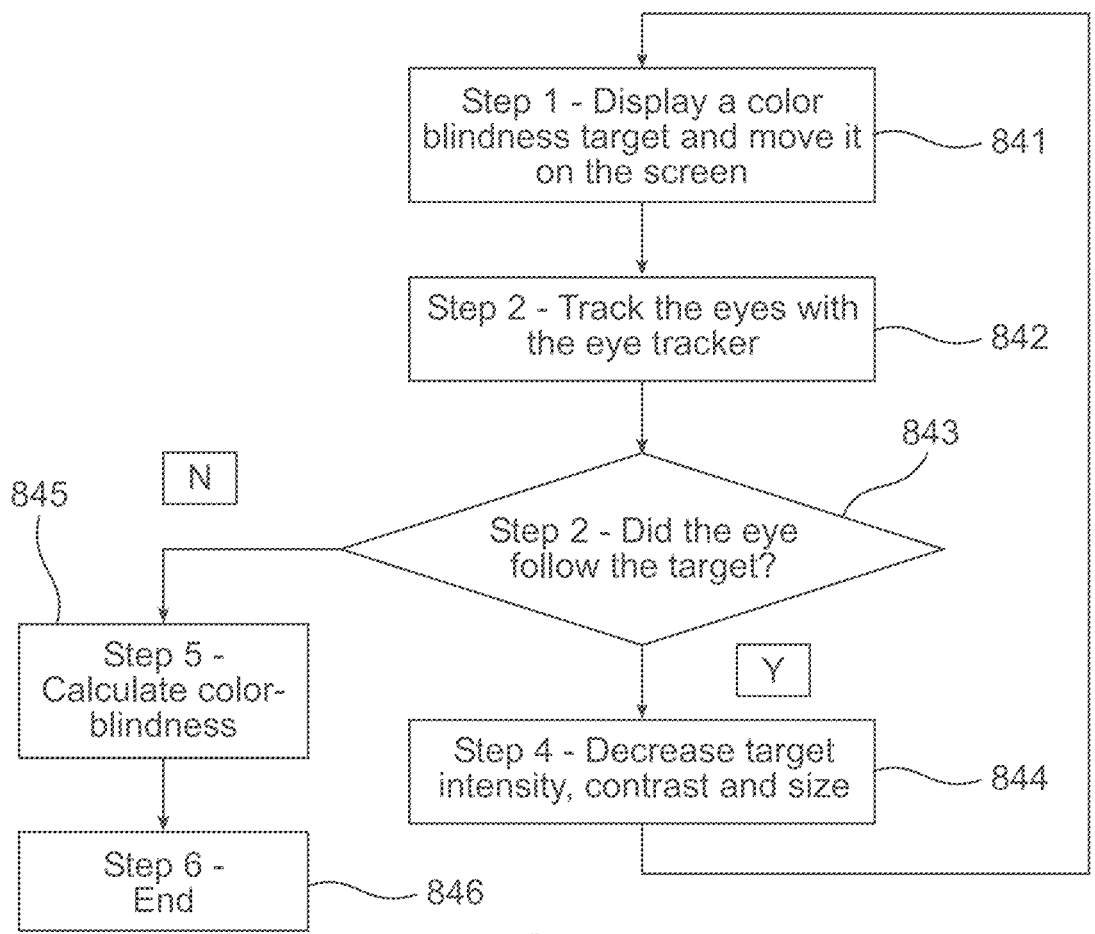
FIG. 35 shows the Color Blindness Test method, Main Process.

FIG. 35 shows the color blindness test main process. The method includes:

Step 1—Display a color blindness target with high intensity, contrast and size (in initialization phase) and move it on the screen. 841
Step 2—Track the eyes with the eye tracker and provide the data to the processor. 842
Step 3—The processor will determine whether the eye see/tracked the target along its path. If the eye was tracking the color blindness target the process will move to step 4. If the eye will not be able to see and/or track the target, the process will go to step 5. 843
Step 4—The color blindness parameters will decrease and go back to step 1. 844
Step 5—The processor will calculate the color blindness score based on the last tracked target color contrast. 845
Step 6—End. 846

The test can be conducted with other images than the geometric shapes by providing more attractive targets for children like animals, cartoon heroes, symbols etc.

Eyes' Dynamics Test

In this test, the apparatus measures several parameters:
- Saccades initiation delays
- Saccades speeds and trajectory
- Smooth pursuit tracking quality
- Vestibulo-ocular reflex
- Optokinetic reflex Saccades Delays, Speeds and Trajectory Measurements In the following pictures we show the display for a single eye. A target will be presented on the display and will abruptly change its position. It will jump from the left down side of the display to the right up position. See FIGS. 36A, 36B.

Figure 36B:
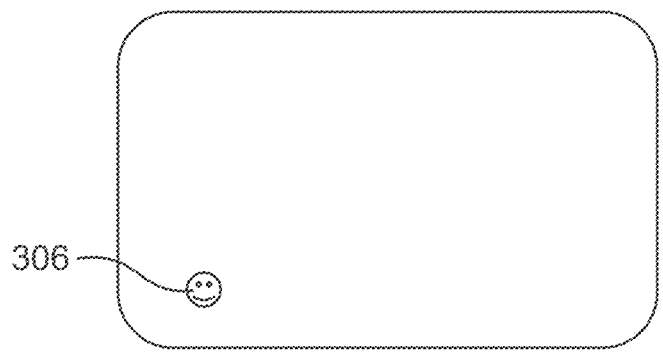
Figure 36B:
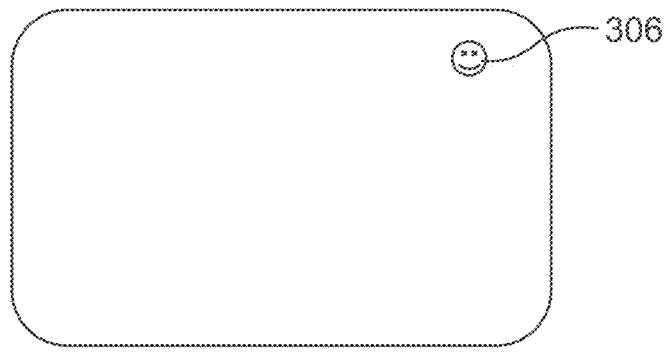

FIGS. 36A, 36B show a Method of Target Stimulus for Saccades Test.

The test image 306 is shown first in one location as shown in FIG. 36A, then in another location as shown in FIG. 36B. The typical movement of the eye for this kind of stimulus is shown in FIG. 37.

Figure 37:
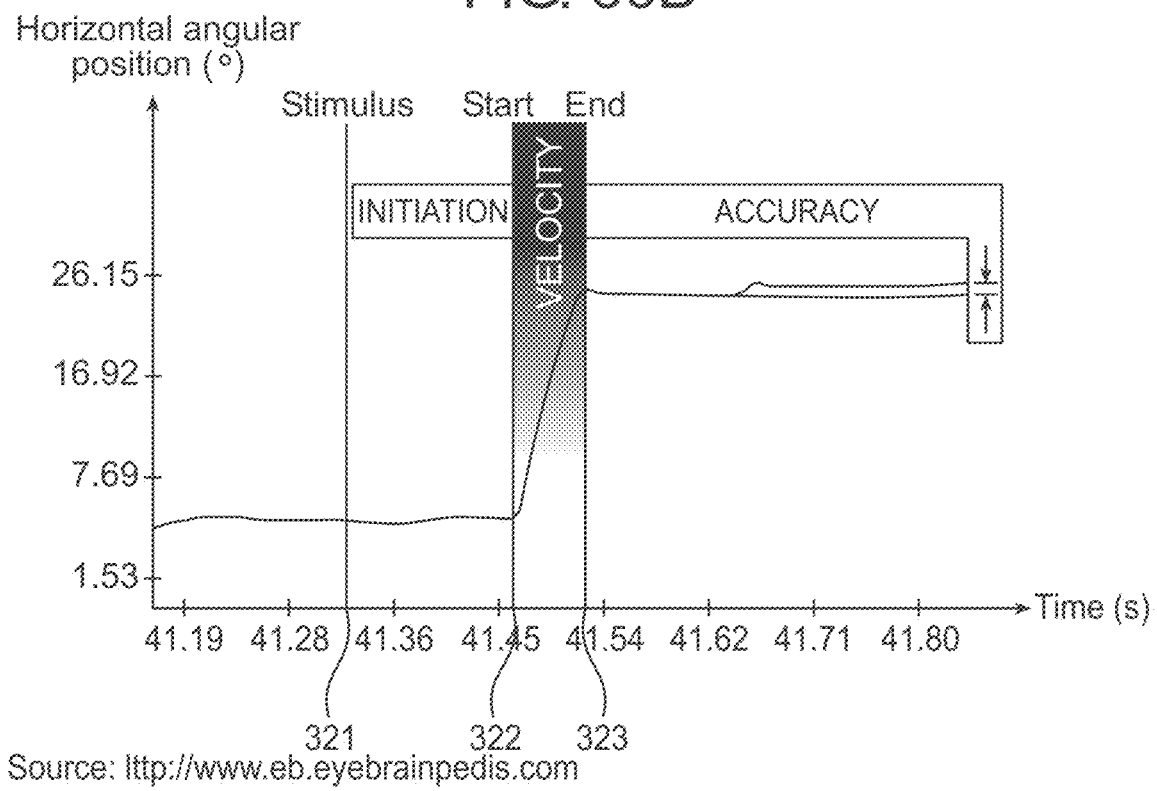
FIG. 37 shows a Typical Saccade Movement Graph.

FIG. 37 shows a Typical Saccade Movement Graph. The graph displays the eye angular position vs. time. During the test, the eye may be stimulated to move horizontally, vertically or in a slant direction.

Initially the test image 306 is displayed in a first location, as shown in FIG. 36A.

After the stimulus is applied at time 321 (the test image 306 is moved to its second location as shown in FIG. 36B), there is a time delay until eye movement begins at time 322. The eye movement ends at time 323, when the eye points at the test image 306 in its second location, as shown in FIG. 36B.

Figure 38A:
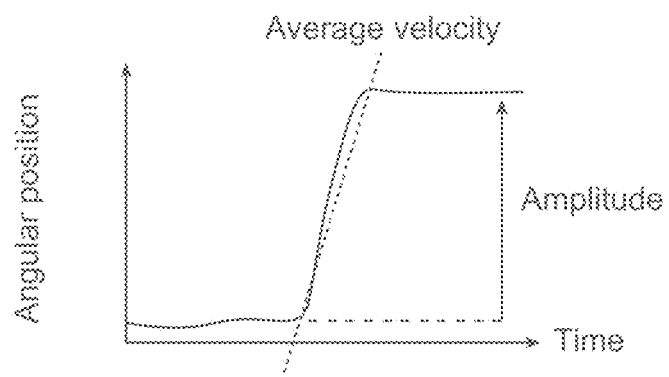
FIGS. 38A (top two frames), 38B (bottom two frames) show a Method of Comparing Between Normal and Slow Saccades Velocity.
Figure 38B:
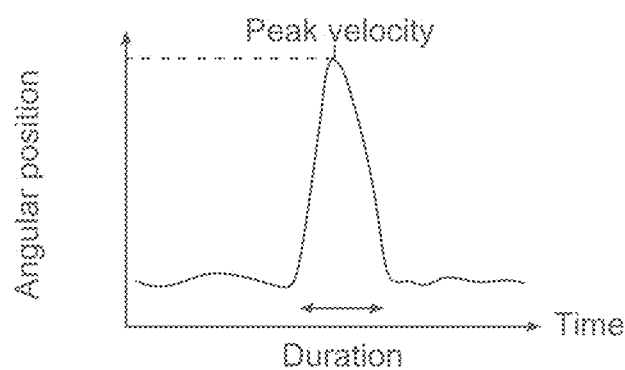

The eye tracker in the embodiment will track the eye and will determine whether the velocities, average and peak, are normal or were improved, deteriorated or unchanged from previous measurements, see FIGS. 38A, 38B.

FIGS. 38A, 38B show a Method of Comparing Between Normal and Slow Saccades Velocity.

FIG. 38A shows a normal eye saccade, with two graphs showing the angle and angular velocity vs. time, respectively.

FIG. 38B shows a slow eye saccade, again with two graphs showing the angle and angular velocity vs. time, respectively. In this case, the angular velocity is smaller than that of the normal eye.

Figure 39A:
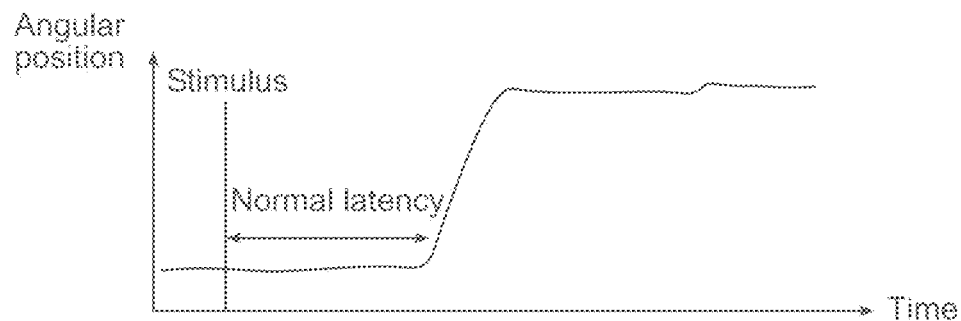
FIGS. 39A, 39B, 39C show results of Latency Measurements.
Figure 39B:
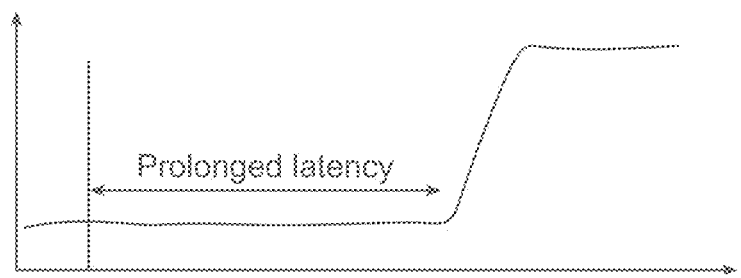
Figure 39C:
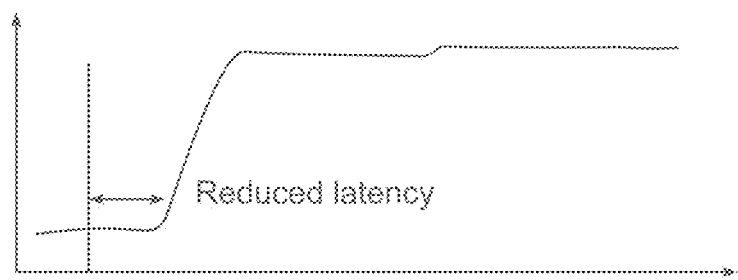

The eye tracker in the embodiment will track the eye and will determine whether the initiation delay (latency) of the saccadic initiation latency is normal, was improved, deteriorated or unchanged from previous measurements, see FIGS. 39A, 39B, 39C.

FIGS. 39A, 39B, 39C show results of Latency Measurements.

The graphs in FIGS. 39A, 39B, 39C illustrate angular eye position vs. time for normal latency, prolonged latency (slow eye movement) and reduced (faster eye movement) latency, respectively.

Figure 40:
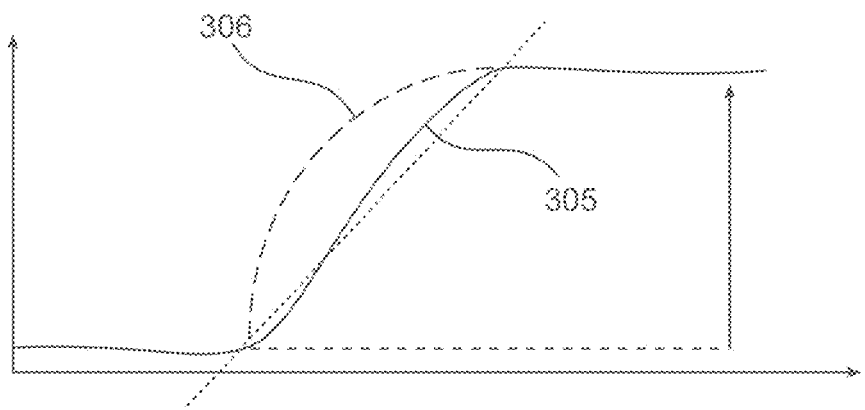
FIG. 40 shows the result of Eye Trajectory Measurements.

In FIG. 40 we can see a normal and abnormal trajectory. The eye tracker in the embodiment will track the trajectory of the eye and will determine whether the eye trajectory is normal, abnormal, was improved, deteriorated or unchanged from previous measurements.

Furthermore, the shape of the abnormal eye trajectory will enable the option to provide a patient's condition e.g. what muscles or nerves, if any, might be impaired.

FIG. 40 shows the result of Eye Trajectory Measurements, illustrating a normal eye angle trajectory 305 and an abnormal trajectory 306.

Smooth Pursuit Tracking Quality Measurements

In the following pictures we show the display for a single eye. In the following pictures the arrow is not a part of the stimulation.

Figure 41:
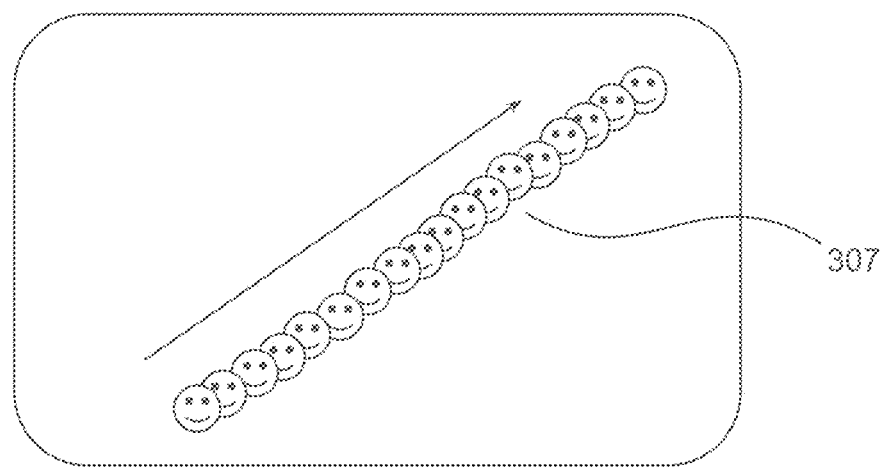
FIG. 41 shows a Target Stimulus movement for Smooth Pursuit Test.

A target will be presented on the display and will move in a constant speed from the left down side of the display to the right up position, see FIG. 41.

FIG. 41 shows a Target Stimulus movement for Smooth Pursuit Test.

The target moves on the display along the path 307.

Figure 42:
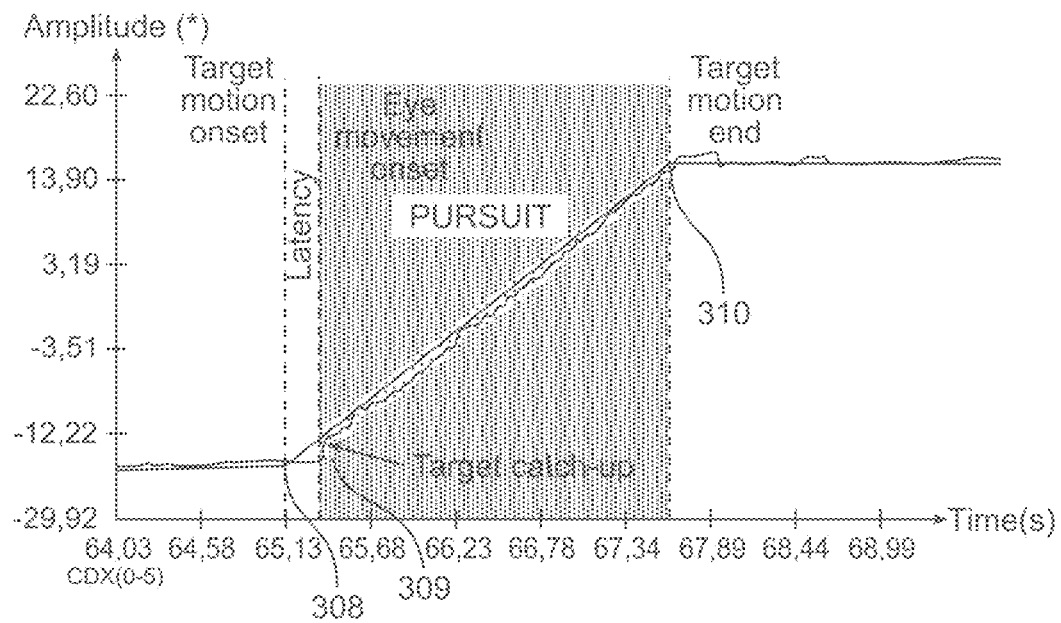
FIG. 42 shows a Smooth Pursuit, Eye Trajectory Measurements.

The typical movement of the eye for this kind of stimulus is shown in FIG. 42.

FIG. 42 shows a Smooth Pursuit, Eye Trajectory Measurements.

The graph shows eye angle variation vs. time, indicating the target motion onset 308, target catch-up 309, then pursuit until the target motion end 310.

Figure 43:
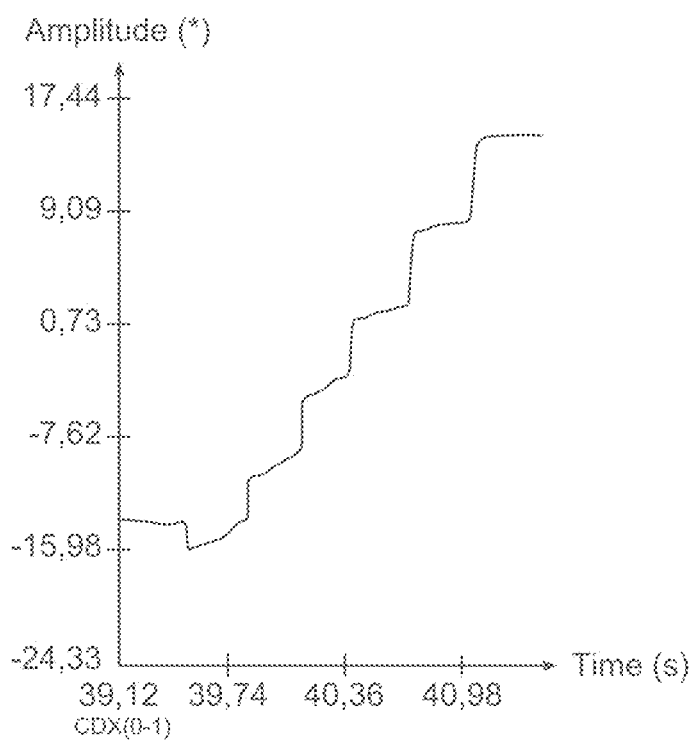
FIG. 43 shows a Smooth Pursuit, Abnormal Trajectory.

As mentioned above for saccades trajectories, the eye tracker in the embodiment will track the trajectory of the eye and will determine whether the trajectory is normal, abnormal, was improved, deteriorated or unchanged from previous measurements. An example of abnormal smooth pursuit eye trajectory is depicted in FIG. 43.

Furthermore, the shape of the abnormal eye trajectory will point out which muscles out of the 6 extra-ocular muscles is malfunctioning.

Vestibulo-Ocular Reflex Measurements

Figure 44A:
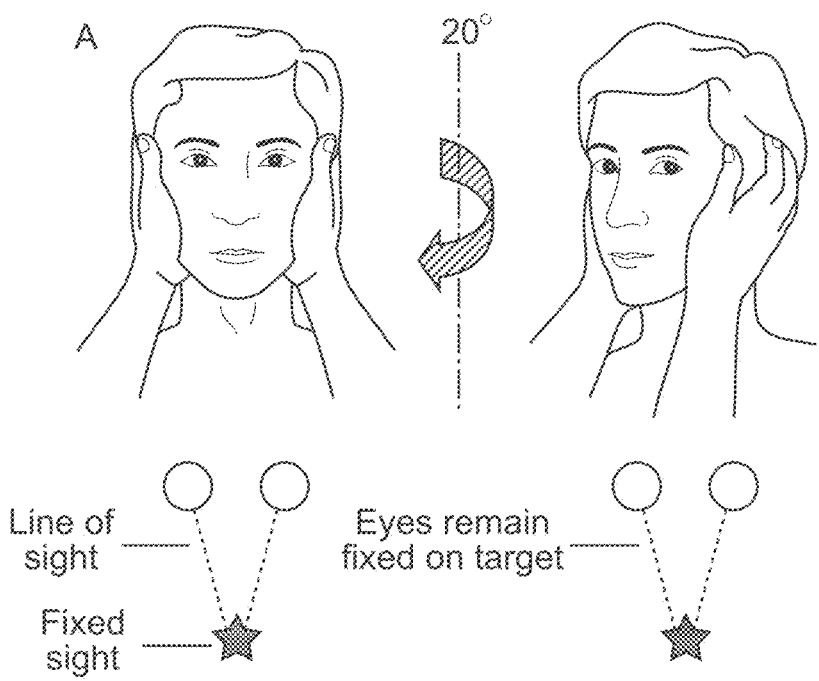
FIGS. 44A, 44B show a Vestibulo-Ocular Reflex Measurements Setup.

A fixed target will be presented for the patient on the embodiment display. The patient head will be abruptly or smoothly rotated, either by himself or by another person to the side, as shown in FIG. 44A. The movements can be horizontally, vertically or any combinations thereof.

In this kind of stimulus, the eyes of a normal patient should remain fixed on the target as shown on the right side of FIG. 44A.

Figure 44B:
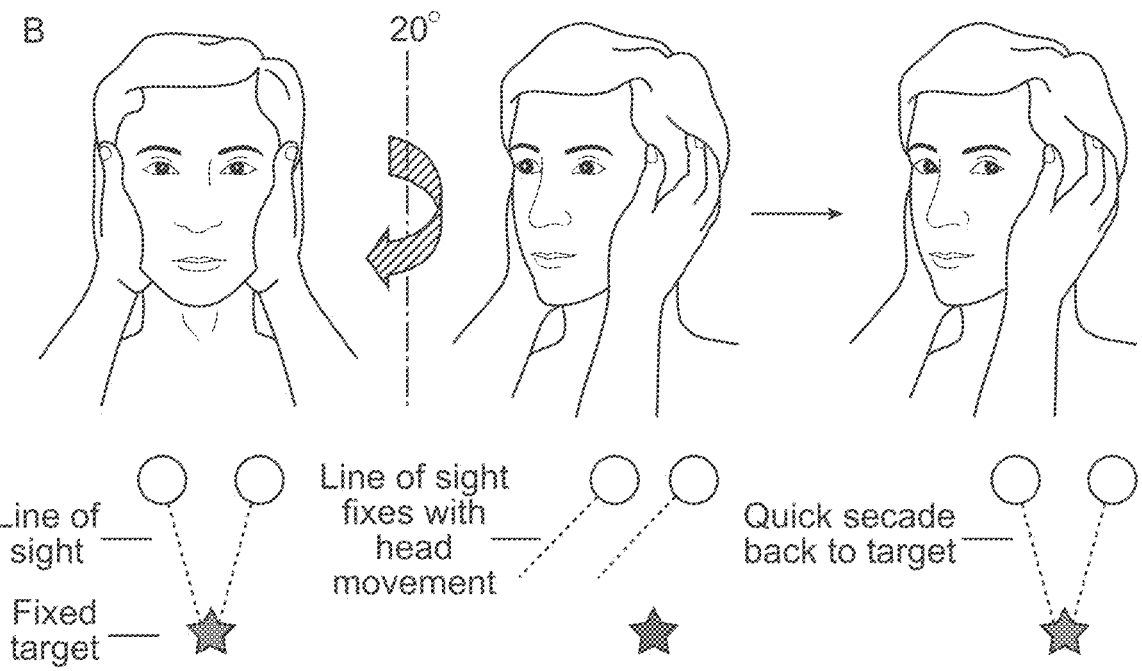

The eye tracker in the embodiment will track the trajectory of the eye and will determine whether the trajectory is normal, abnormal, was improved, deteriorated or unchanged from previous measurements. An example of abnormal eyes trajectory is depicted on the FIG. 44B. In case of sinusoidal head rotation, a normal eye rotation in relation to the head will be as shown in FIG. 45.

Figure 45:
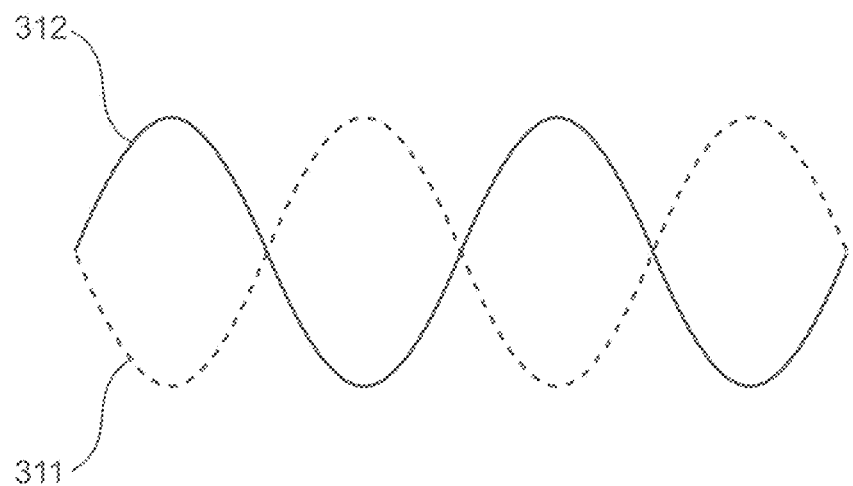
FIG. 45 shows a Vestibulo-Ocular Reflex Measurements for Sinusoidal Head Movement.

FIG. 45 shows a Vestibulo-Ocular Reflex Measurements for Sinusoidal Head Movement, indicating head angle movement 311 and eye angle movement 312 vs. time.

In the above mentioned cases, a head position tracker will add accuracy to the apparatus. This head tracker could be a commercial device type used in video games and virtual reality. Furthermore, the shape of the abnormal eyes trajectory will help the professional in the diagnostics of the reason for the case, either the ocular or the vestibular apparatus.

Another embodiment uses both remote eye trackers and near eye trackers, to compute the head movements therefrom. The remote eye trackers measures eyes line of sight direction relative to a fixed platform, whereas near eye trackers measures eyes line of sight direction relative to the patient's face. The difference between these measurements gives the direction of the patient's head.

Optokinetic Reflex Measurements

The optokinetic reflex is a combination of a saccade and smooth pursuit eye movements. It is seen when an individual follows a moving object with his eyes, which then moves out of the field of vision at which point their eye moves back to the position it was in when it first saw the object and so on. It is used to test visual acuity in preverbal and young children.

Figure 46:
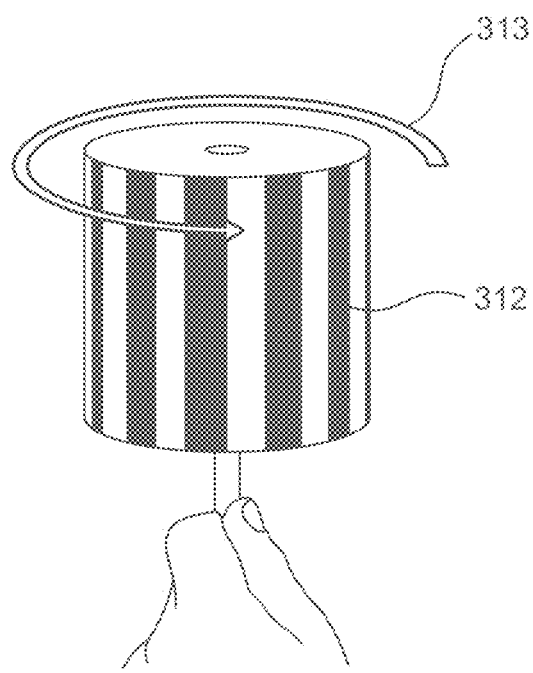
FIG. 46 shows an Optokinetic Reflex Measurements Drum.

A standard apparatus for this measurement consist of a rotatable drum with vertical line as shown in FIG. 46.

FIG. 46 shows an Optokinetic Reflex Measurements Drum 312. The drum 312 may be rotated about a longitudinal axis as shown with arrow 313.

The drum is rotated and the patient track the stripes from left to right with smooth pursuit movement. As the eyes reaches the right gaze limit, the eyes return to their initial position with a saccade movement and so on.

The existing drum is a mechanical device on which is difficult to change spatial frequency and contrast of the stripes or to keep required speed. Our embodiments will present the targets not on a drum but on the display. The stripes will continuously move, for example, from left to right, see FIG. 47.

Figure 47:
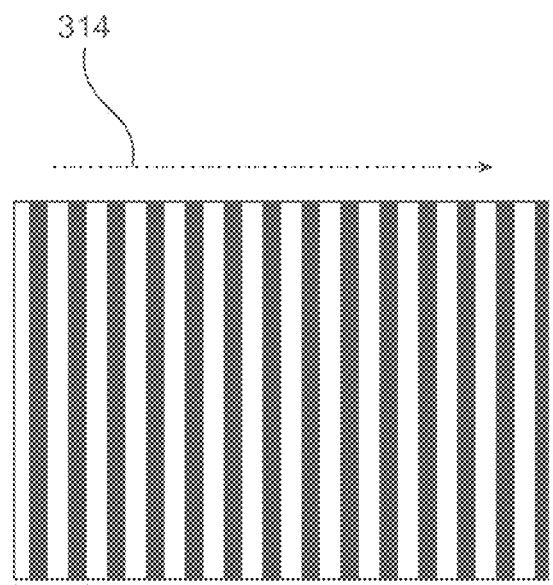
FIG. 47 shows an Optokinetic Reflex Measurements screen Display.

FIG. 47 shows an Optokinetic Reflex Measurements screen Display. The vertical stripes presented on screen move continuously in a horizontal direction as indicated with the arrow 314.

The eye tracker in the embodiment will track the trajectory of the eye and will determine whether the trajectory is normal, abnormal, was improved, deteriorated or unchanged from previous measurements. An example of a normal trajectory is depicted in FIG. 48.

Figure 48:
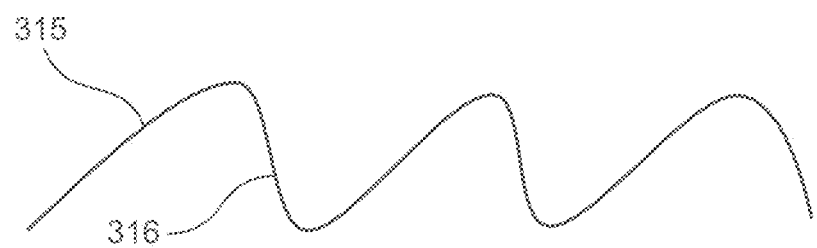
FIG. 48 shows a Normal Optokinetic Eye Movement.

FIG. 48 shows a Normal Optokinetic Eye Movement, indicating eye angle movement vs. time. The graph shows alternating zones of smooth pursuit 315 and saccade 316, responsive to eyes excitation with the drum of FIG. 46 or the screen of FIG. 47.

Pursuit 315 occurs while the eye follows a horizontally moving stripe; saccade 317 occurs when the eye jumps to another stripe to follow.

Figure 49:
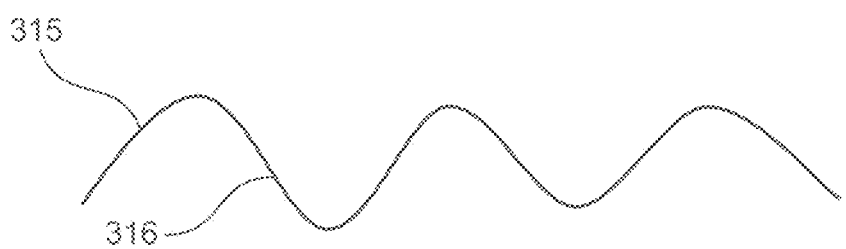
FIG. 49 shows an abnormal Optokinetic Eye Movement.

An abnormal eye trajectory, in which the saccades are too slow, is depicted in FIG. 49.

FIG. 49 shows an abnormal Optokinetic Eye Movement, again indicating eye angle movement vs. time. The graph shows alternating zones of smooth pursuit 315 and saccade 316, responsive to eyes excitation with the drum of FIG. 46 or the screen of FIG. 47.

The difference is that in this case, the saccade 316 is slow, indicating a problem with the eye in performing this task.

Another way for the use of optokinetic reflex is the to analyze and the visual acuity and contrast sensitivity.

Figure 50:
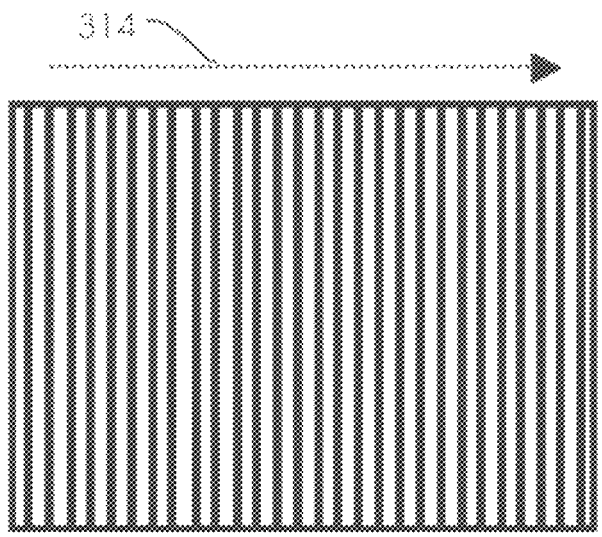
FIG. 50 shows a screen with higher spatial frequency stripes.
Figure 51:
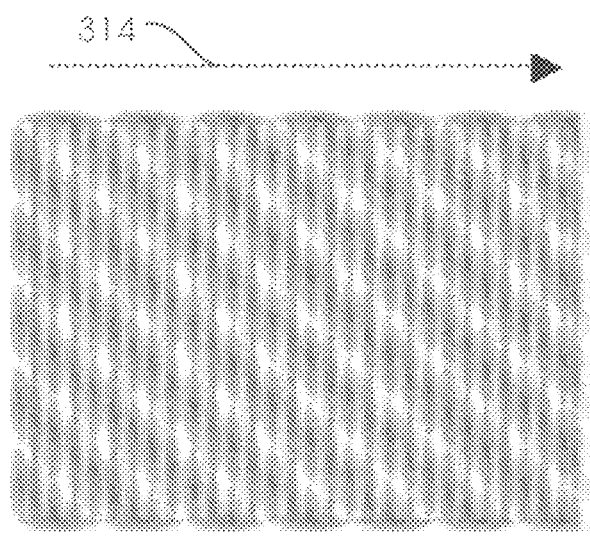
FIG. 51 shows a screen with lower contrast stripes.

This is done by gradually increasing the speed or the spatial frequency of the stripe as seen in FIG. 50 or decreasing the contrast of the stripe as seen in FIG. 51, until the specialist observes that the patient stopped tracking the stripes. Alternatively, the processor can detect automatically that the patient stopped tracking the stripes.

In preferred embodiments, the eye tracker will track the trajectory of the eyes.

The stripes become harder to track by increasing the spatial frequency (the stripes become progressively finer or closer together and/or by increasing speed), by decreasing the contrast and so on until the eyes will not be able to continue tracking. The eye tracker will determine when the eyes stop tracking.

The processor will calculate the visual acuity based on standard tables that correlate that Stripe's frequency, density and contrast to the relevant visual acuity. This information is especially pertinent to visual acuity measurements in pre-verbal children.

FIG. 50 shows a screen with higher spatial frequency stripes. The stripes move continuously in a horizontal direction as indicated with the arrow 314.

The difference from the stripes shown in FIG. 47 is the higher spatial frequency of the stripes, which present a more difficult challenge to the eye under test.

Reading Speed

By tracking the speed of reading (typically possible from the age of 6 or so) as measured by the eye tracker, important parameters about the reading factors such as fixation stability and saccade accuracy could be gathered in addition to the reading speed measurement by itself (which is an important parameter to the child cognitive development). The reading speed will be determined with a built in microphone and voice recognition software (well known in the art) that will compare the reading of the patient with the displayed words for correctness.

Pupil Tests

Pupil tests can point out various problems such as retinal, neurologic or other diseases. The eye trackers provide instantaneous pupil size and location and the apparatus performs the test according to the following table. If normal results are not obtained, the apparatus informs the operator about the discrepancies.

| Test | Stimulation | Normal Results |
| --- | --- | --- |
| Pupil shape and size at rest | Normal light intensity on display | Pupils should be round, same size, symmetrical and centered within the iris |
| Direct response | High light intensity to single eye | Constriction of the illuminated pupil |
| Consensual response | High light intensity to single eye | Constriction of opposite pupil |
| Accommodation response | Near view target | Constriction of pupils |

Screening

The apparatus will be used for screening people, especially small children and infants for vision deficiency.

All kinds of proposed embodiments can be used to perform the task. Following are example of some task:
  Visual acuity
  Strabismus angle and extent of heterophoria
  Extent of stereopsis
  Color Blindness Test
  Convergence insufficiency diagnosis
  Eye movements: saccades speeds, trajectory and reaction time, vestibulo-ocular reflex measurements
  Optokinetic reflex measurements
  Reading speed
  Pupil testing.

The apparatus performs the same tasks as for monitoring and assessment (see description above) compares it to a standard model for reporting of possible problems that requires more thorough examination by a specialist.

Since the apparatus would be used in such a case for screening purposes by non-specialist operators, the apparatus and application might be modified in such a way as to maximize speed and comfort of the test on the expense of accuracy.

FIG. 51 shows a screen with lower contrast stripes. The stripes move continuously in a horizontal direction as indicated with the arrow 314.

The difference from the stripes shown in FIG. 47 is the lower contrast of the stripes, which present a more difficult challenge to the eye under test.

The moving stripes shown in FIGS. 47, 50 and 51 may be generated on an electronic screen (display) in a test or treatment method according to the present invention. It is to be understood that variations of these stripes may be generated as well, for example horizontal stripes moving in a vertical direction, slant stripes moving in a direction normal to that of the stripes, stripes in color, etc.

Adaptive Method for Screening, Treatment, Monitoring and/or Assessment of Visual Impairments Note: The method can be applied to any of the embodiments of the apparatus disclosed in the present invention.

The method includes:

a. defining a starting point, wherein differences between a patient's eyes are completely, or as closely as practically possible, corrected, to enable two identical or similar images to be transferred to the brain from the patient's eyes. The required correction is based on results of measuring the characteristics of the patient's eyes.

b. defining an ending point, wherein there is no correction applied to any of the patient's eyes. The ideal or ultimate goal of the treatment is to correct the defects in the patient's eyes, so he/she can function without an external support apparatus. The goal may or may not be reached, depending on the patient capabilities; however, in any case the invention helps in improving a patient's vision or at least to prevent or minimize a possible deterioration following an operation, for example.

c. defining a screening, treatment, monitoring and/or assessment plan, for initially applying correction to images according to the starting point, then gradually reducing the correction, at a controlled and predetermined rate, towards the ending point; and d. applying the plan to images presented to the patient's eyes, while monitoring patient's performance.

Further optional improvements to the method may include:

e. Adjusting the rate of change of the correction responsive to results of monitoring the patient's performance. That is, if monitoring shows the patient's progress is slower than initially estimated, then the rate of change may be reduced, so we aim at a more modest, but attainable, goal.

f. The correction may includes a movement of the image vertically and/or horizontally, changing the magnification of the image (zoom in or zoom out), and/or rotation of the image.

g. Changing the plan for screening, treatment, monitoring and/or assessment responsive to results of monitoring the patient's response to applying the plan thereto. This step may be applied if monitoring shows that the patient is not responding to the initial planned strategy. A different strategy may be tried out. It is impossible to know in advance how a patient may respond to treatment.

h. Defining a range of desired rate of improvement with minima and maxima, during monitoring comparing actual patient's performance with the desired rate of improvement, and issuing a report or a warning if the actual performance exceeds the range of desired rate of improvement. This step may be applied in case of failure of the previous attempts at adapting the treatment to that patient. Maybe a professional may devise a better plan for that patient, maybe additional tests are required or an intervention, etc.

Method 2 for Convergence Insufficiency Diagnosis, Main Process

Figure 52:
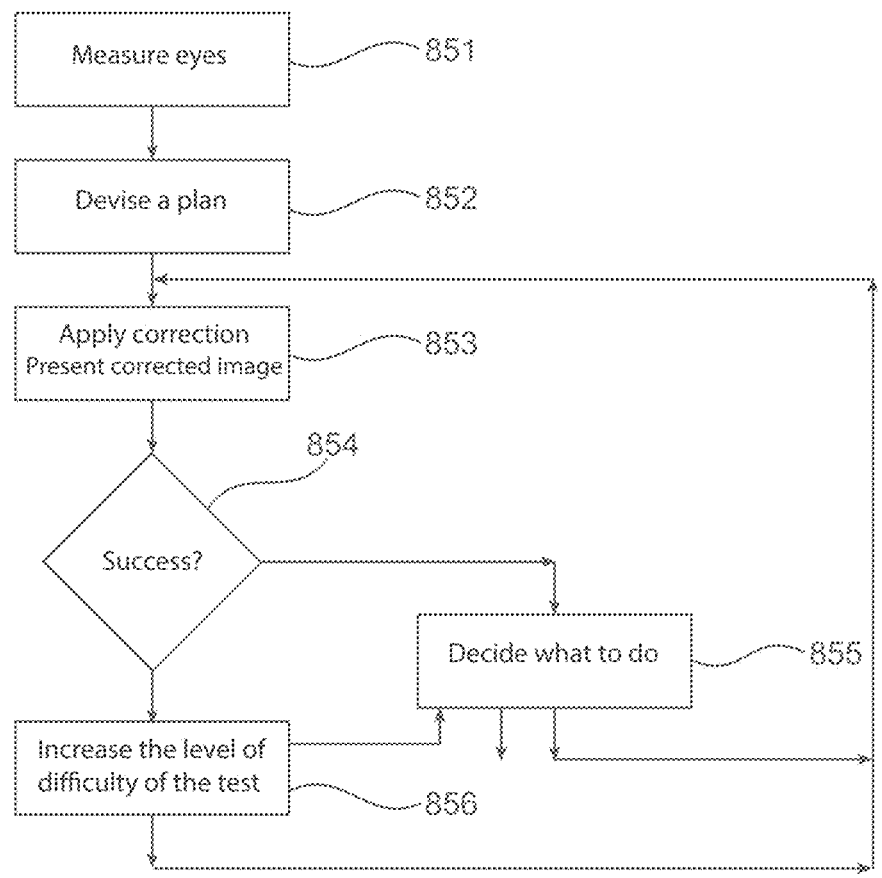
FIG. 52—Method 2 for convergence insufficiency diagnosis, main process.

FIG. 52 shows Method 2 for convergence insufficiency diagnosis. The method includes:

1. Measure patient's eyes. Peformed by professional, the measurement preferably includes as many as possible ailments of the eye. Each eye is measured separately, and the performance of both eyes together is measured as well. 851
2. Devise a convergence insufficiency diagnosis plan. 852
The plan includes:
   a. defining a starting point, wherein differences between a patient's eyes are completely, or as closely as practically possible, corrected, to enable two identical or similar images to be transferred to the brain from the patient's eyes;
   b. defining an ending point, wherein there is no correction applied to any of the patient's eyes;
   c. defining a diagnosis plan, for initially applying correction to images according to the starting point, then gradually reducing the correction, at a controlled and predefined rate, towards the ending poin.
   d. set the initial values for the correction to the images presented to the eyes, according to the starting point of the plan.
3. Perform a stage of the diagnosis process:
   a. apply a correction to the images presented to the eyes, according to the present values for correction, and present the images to the patient's eyes. 853
   b. challenge the eyes, for example by moving a picture across the screen;
   c. measure, using eye trackers, whether the eyes follow the movement.
   d. Log/record the results of the measurement, together with the relevant parameters.
4. Success? Do patient's eyes perform the required task? 854
5. Decide what to do: 855
   a. If failure at the initial stage—the first time the test is applied to the patient's eyes, the plan should be revised and/or the equipment checked:
Maybe the initial images correction is not satisfactory, probably because of insufficient testing of the patient's eyes. Maybe the test equipment needs to be verified and/or adjusted. Exit test.
   b. If failure after just one change in the initial parameters, maybe the increment was too large. The test may be restarted, with a slower progress—a smaller change in the image processing after each iteration. Continue test, Goto 853.
   c. If failure after more than one change in the initial parameters, then it is indicative of the patient's convergence insufficiency (CI). From the last value of parameters where patient's eyes did perform the required task, compute the patient's CI. Exit test.
   d. If the test reached the ending point in the plan (this is indicative of a perfectly normal vision, without any aids)—report this fact, and Exit test.
6. Increase the level of difficulty of the test, by reducing the correction of the images presented to the patient's eyes. 856. The reduction—according to the plan devised in 852.
If the test reached the ending point in the plan (this is indicative of a perfectly normal vision, without any aids), GOTO End 855.

It will be recognized that the foregoing is but one example of an apparatus and method within the scope of the present invention and that various modifications will occur to those skilled in the art upon reading the disclosure set forth hereinbefore, together with the corresponding drawings.

The invention claimed is:

1. An apparatus for treatment of amblyopia, comprising:

electronic means comprising image generating means, digital image processing means, eye tracker means for measuring a direction of the line of sight of an eye of a patient having an amblyopic eye and a non-amblyopic eye, said eye tracker means comprising a single eye tracker, and display means for presenting a dichoptic pair of images to both of the patient's eyes;

wherein said digital image processing means are configured for creating an area with a controlled measure of image degradation in an image displayed to a non-amblyopic eye of a patient, where the location of said degraded area is moved responsive to a measured direction of the line of sight of one of the eyes of the patient.

2. The apparatus of claim 1, wherein said digital image processing means are configured so that said location of said degraded area is moved responsive to a measured direction of the line of sight of the non-amblyopic eye of the patient.

3. The apparatus according to claim 1, wherein said degraded area is so located on the display means as to be presented on a fovea of the non-amblyopic eye.

4. The apparatus according to claim 1, wherein said degraded area is so located on the display means as to be presented on a macula of the non-amblyopic eye.

5. The apparatus according to claim 1, wherein in said degraded area, the degree of image degradation is not uniform.

6. The apparatus according to claim 5, wherein in said degraded area, the degradation is stronger in the center of said area and is gradually reduced towards the edges of said area, to provide a smooth transition.

7. The apparatus according to claim 1, wherein said location of said degraded area is moved on the screen responsive to the measured direction of the line of sight of the non-amblyopic eye.

8. A method for treatment of amblyopia in a patient having an amblyopic eye and a non-amblyopic eye, comprising:

presenting a dichoptic pair of images to the patient's eyes on a display, including applying digital image processing means for creating an area with a controlled measure of image degradation to the one image of said dichoptic pair of images displayed to the non-amblyopic eye, where the location of said degraded area on the display is moved responsive to a measured direction of the line of sight of at least one of the two eyes, wherein said measured direction of the line of sight of at least one of the two eyes is performed using a single eye tracker thereby measuring the line of sight of a single one of the two eyes.

9. The method of claim 8, wherein said measured direction of the line of sight is of the non-amblyopic eye.

10. The method according to claim 8, wherein said degraded area is so located on the display so as to be presented on a fovea of the non-amblyopic eye.

11. The method according to claim 8, wherein said degraded area is so located on the display so as to be presented on a macula of the non-amblyopic eye.

12. The method according to claim 8, wherein in said degraded area, the degree of image degradation is not uniform.

13. The method according to claim 12, wherein in said degraded area, the degradation is stronger in the center of the area and is gradually reduced towards the edges of the area, to provide a smooth transition.

* * * * *